US010851160B2

(12) United States Patent
Baumert et al.

(10) Patent No.: US 10,851,160 B2
(45) Date of Patent: Dec. 1, 2020

(54) HUMANIZED ANTI-CLAUDIN-1 ANTIBODIES AND USES THEREOF

(71) Applicants: INSERM (Institut National de la Santé et de la Recherche Médicale), Paris (FR); Université de Strasbourg, Strasbourg (FR); Chu Strasbourg, Les Hôpitaux Universitaires de Strasbourg, Strasbourg (FR)

(72) Inventors: Thomas Baumert, Strasbourg (FR); Rajeevkumar Tawar, Oxfordshire (GB)

(73) Assignees: Institut National de la Sante et de la Recherche Medicale, Paris (FR); Universite de Strasbourg, Strasbourg (FR); Chu Strasbourg, les Hopitaux Universitaires de Strasbourg, Strasbourg (FR)

( * ) Notice: Subject to any disclaimer, the term of this patent is extended or adjusted under 35 U.S.C. 154(b) by 0 days.

(21) Appl. No.: 16/086,934

(22) PCT Filed: Mar. 21, 2017

(86) PCT No.: PCT/EP2017/056703
§ 371 (c)(1),
(2) Date: Sep. 20, 2018

(87) PCT Pub. No.: WO2017/162678
PCT Pub. Date: Sep. 28, 2017

(65) Prior Publication Data
US 2019/0100586 A1    Apr. 4, 2019

(30) Foreign Application Priority Data

Mar. 22, 2016  (EP) .................................... 16305317

(51) Int. Cl.
*C07K 16/28* (2006.01)
*A61P 31/14* (2006.01)
*A61P 1/16* (2006.01)
*C12N 15/62* (2006.01)
*A61K 39/00* (2006.01)

(52) U.S. Cl.
CPC ............ *C07K 16/28* (2013.01); *A61P 1/16* (2018.01); *A61P 31/14* (2018.01); *C12N 15/62* (2013.01); *A61K 2039/505* (2013.01); *A61K 2039/545* (2013.01); *C07K 2317/24* (2013.01); *C07K 2317/55* (2013.01); *C07K 2317/565* (2013.01); *C07K 2317/567* (2013.01)

(58) Field of Classification Search
None
See application file for complete search history.

(56) References Cited

FOREIGN PATENT DOCUMENTS

| WO | 2010/034812 A1 | 4/2010 |
|---|---|---|
| WO | 2010/039801 A2 | 4/2010 |

OTHER PUBLICATIONS

Owen et al. (Journal of Immunological Methods, 1994, p. 149-165).*
Mailly et al., "Clearance of persistent hepatitis C virus infection in humanized mice using a claudin-1-targeting monclonal antibody," Nature Biotechnology, 33: 549-554 (2015).
Yamashita et al., "Discovery of Anti-Claudin-1 Antibodies as Candidate Therapeutics against Hepatitis C Virus," Journal of Pharmacology and Experimental Therapeutics, 353: 112-118 (2015).
Paciello et al., "Novel human anti-cluadin 1 mAbs inhibit hepatitis C virus infection and may synergize with anti-SRB1 mAb," Journal of General Virology, 97: 82-94 (2016).
Safdari et al., "Antibody humanization methods—a review and update," Biotechnology and Genetic Engineering Reviews, 29: 175-186 (2013).
International Search Report issued in corresponding International Patent Application No. PCT/EP2017/056703 dated Jun. 8, 2017.
Written Opinion issued in corresponding International Patent Application No. PCT/EP2017/056703 dated Jun. 8, 2017.

* cited by examiner

*Primary Examiner* — Agnieszka Boesen
(74) *Attorney, Agent, or Firm* — Morgan, Lewis & Bockius LLP

(57) ABSTRACT

The present invention relates to humanized anti-claudin-1 antibodies and uses thereof. Hepatitis C virus infection is a leading cause of chronic liver disease and a major indication for liver transplantation. The tight junction protein claudin-1 (CLDN1) is an essential entry factor for HCV and a promising target for therapy. For clinical development, the inventors have humanized a rat anti-CLDN1 antibody produced by genetic immunization that prevent HCV infection and also cure chronically infected human liver chimeric mice. The lead humanized anti-CLDN1 antibody (H3L3) pan-genotypically inhibited HCV pseudoparticle infection of primary human hepatocytes (PHH) without detectable escape. H3L3 efficiently inhibited infection by diverse HCV genotype 3 strains and exhibited marked synergy with direct-acting antivirals (DAAs). The inventors also demonstrate that anti-CLDN1 H3L3 cures persistent HCV infection in human-liver chimeric uPA-SCID mice in monotherapy. Thus, the present invention relates to humanized anti-claudin-1 antibodies and uses thereof, in particular for the prevention and treatment of hepatitis C virus infection, virus-induced liver diseases, hepatocellular carcinoma (HCC), nonalcoholic fatty liver disease (NAFLD) and non-alcoholic steatohepatitis (NASH).

Figure 2:
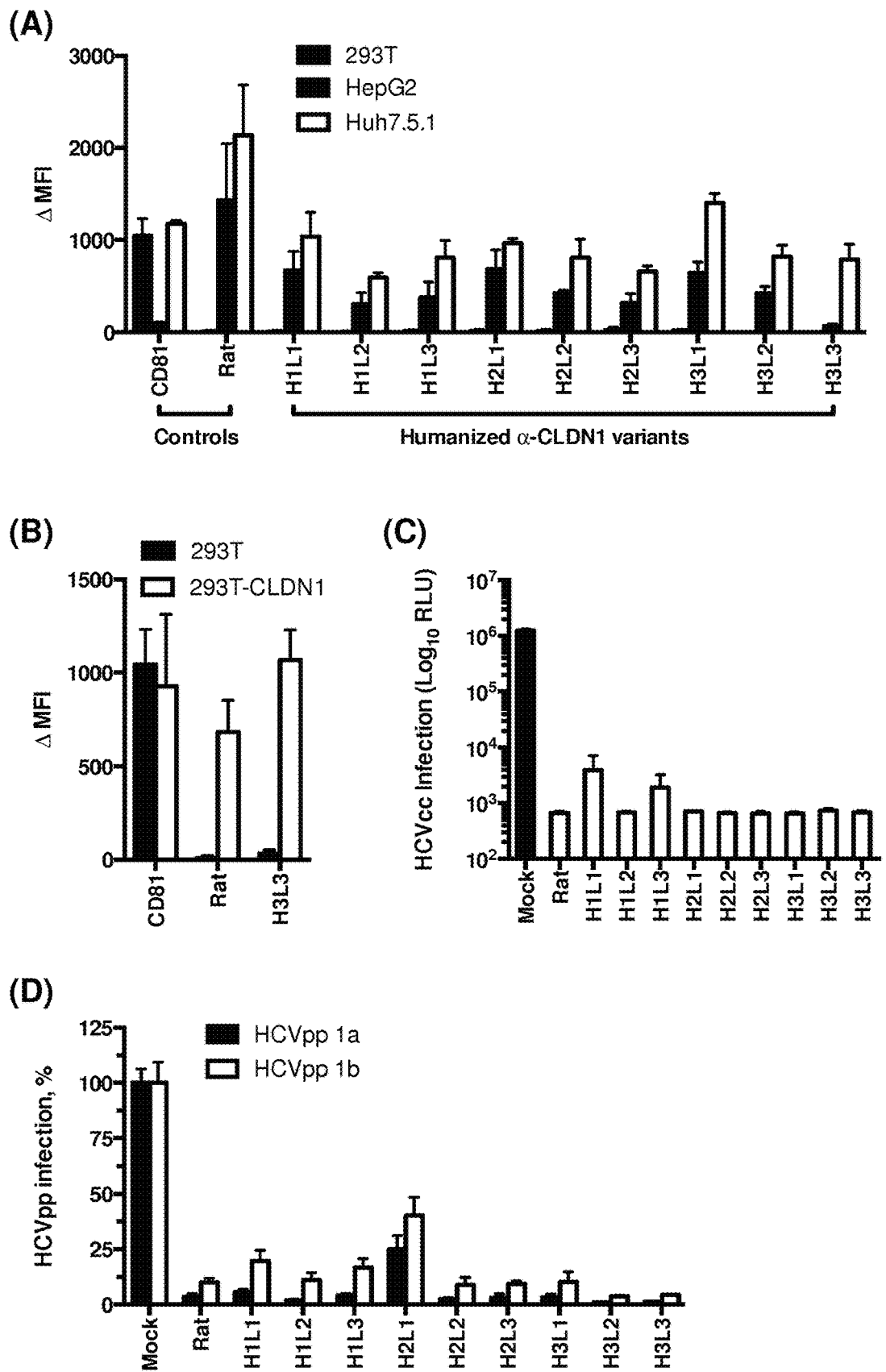

12 Claims, 6 Drawing Sheets
Specification includes a Sequence Listing.

(A)

```
                                FR1              CDR1      FR2              CDR2
OM-7D3-B3 VH    EVQLVESGGGLVQPGRSLKLSCLGSGFSFSSYGMNWIRQAPGKGLEWVASISPSGSYFYY
IGHV5-34*01     EVQLVESGGGLVQPGRSLKLSCVASGFTFSDYRMNWIRQAPGKGLEWVASISSSSSYIYY
                                FR3                    CDR3      J-region
                ADSVKGRFTISRENAKNTLYLQMTSLRAEDTALYYCARLPGFNPPFDHWGQGVVVTVSS
                ADTVKG-FTISRDNAKDTLYLQMTSLRSEDTALYYCAR-----DYFDYWGQGVMVTVSS FR1              CDR1      FR2              CDR2
OM-7D3-B3 VL    NTVMTQSPTSMFMSVGDRVTMNCKASQNVGGNVDWYQWKPGQSPKLLMYGASNRYTGVPD
IGKV6S11*01     NTVMTQSPTSMFISVGDRVTMNCKASQNVGTNVDWYQQKTGQSPKLLIYGASNRYTGVPD RFRGSGSGTDFTLTISNMQTEDLAVYYCLQYKNNPWTFGGGTKVELK
                RFTGSGSGTDFTLTISNMQAEDLAVYYCLQYNYNPWTFGGGTKLELK
```

Figure 1A (B)

```
                                FR1              CDR1      FR2              CDR2
OM-7D3-B3 VH    EVQLVESGGGLVQPGRSLKLSCLGSGFSFSSYGMNWIRQAPGKGLEWVASISPSGSYFYY
IGHV3-21*01     EVQLVESGGGLVKPGGSLRLSCAASGFTFSSYSMNWVRQAPGKGLEWVSSISSSSSYIYY
Humanized H1    EVQLVESGGGLVKPGGSLRLSCAASGFSFSSYGMNWVRQAPGKGLEWVSSISPSGSYFYY
Humanized H2    QVQLVESGGGVVQPGRSLRLSCAASGFSFSSYGMNWVRQAPGKGLEWVTSISPSGSYFYY
Humanized H3    QVQLVESGGGVVQPGRSLRLSCLGSGFSFSSYGMNWVRQAPGKGLEWVASISPSGSYFYY
                                FR3                    CDR3      J-region
                ADSVKGRFTISRENAKNTLYLQMTSLRAEDTALYYCARLPGFNPPFDHWGQGVVVTVSS
                ADSVKGRFTISRDNAKNSLYLQMNSLRAEDTAVYYCAR-----DAFDVWGQGTMVTVSS
                ADSVKGRFTISRDNAKNSLYLQMNSLRAEDTAVYYCARLPGFNPPFDHWGQGTLVTVSS
                ADSVKGRFTISRDNSKNTLYLQMNSLRAEDTAIYYCARLPGFNPPFDHWGQGTLVTVSS
                ADSVKGRFTISRDNSKNTLYLQMTSLRAEDTAIYYCARLPGFNPPFDHWGQGTLVTVSS FR1              CDR1      FR2              CDR2
OM-7D3-B3 VL    NTVMTQSPTSMFMSVGDRVTMNCKASQNVGGNVDWYQWKPGQSPKLLMYGASNRYTGVPD
IGKV3-15*01     EIVMTQSPATLSVSPGERATLSCRASQSVSSNLAWYQQKPGQAPRLLIYGASTRATGIPA
Humanized L1    DIQMTQSPATLSVSPGERATLSCKASQNVGGNVDWYQWKPGQAPRLLIYGASNRYTGIPA
Humanized L2    DIQMTQSPSSLSASVGDRVTITCKASQNVGGNVDWYQWKPGKAPKLLIYGASNRYTGVPS
Humanized L3    DIQMTQSPSSLSASVGDRVTITCKASQNVGGNVDWYQWKPGKAPKLLIYGASNRYTGVPD
                                FR3              CDR3    J-region
                RFRGSGSGTDFTLTISNMQTEDLAVYYCLQYKNNPWTFGGGTKVELK
                RFSGSGSGTEFTLTISSLQSEDFAVYYCQQYNNWPWTFGQGTKVEIK
                RFRGSGSGTEFTLTISSLQSEDFAVYYCLQYKNNPWTFGQGTKVEIK
                RFRGSGSGTDFTLTISSLQPEDVATYYCLQYKNNPWTFGQGTKVEIK
                RFRGSGSGTDFTLTISSLQPEDVATYYCLQYKNNPWTFGGGTKVEIK
```

Figure 1B (A)
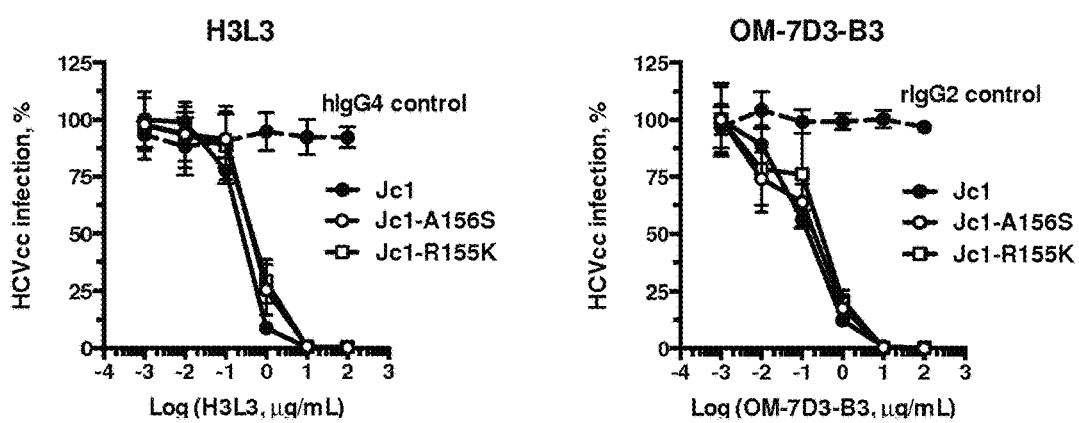
(B)
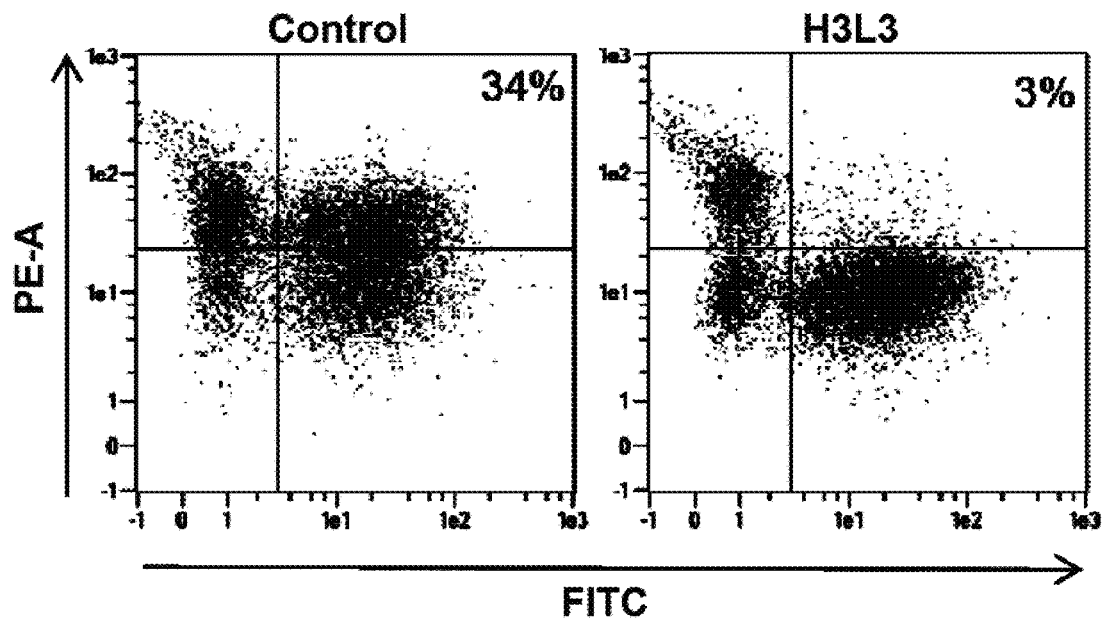
(C)
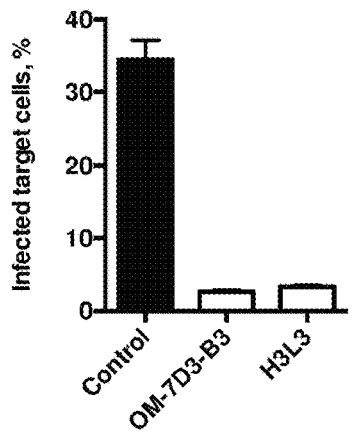
Figure 3A-C (A)
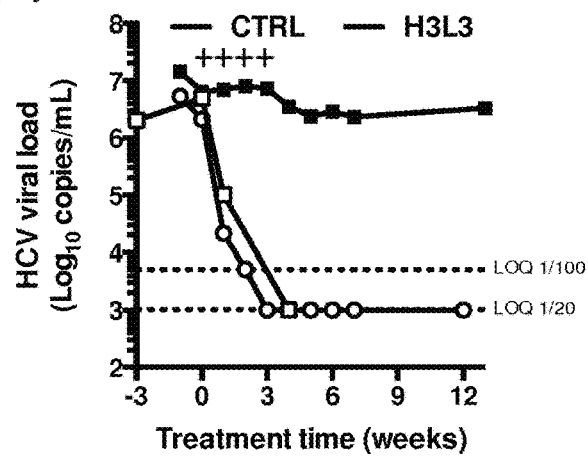
(B)
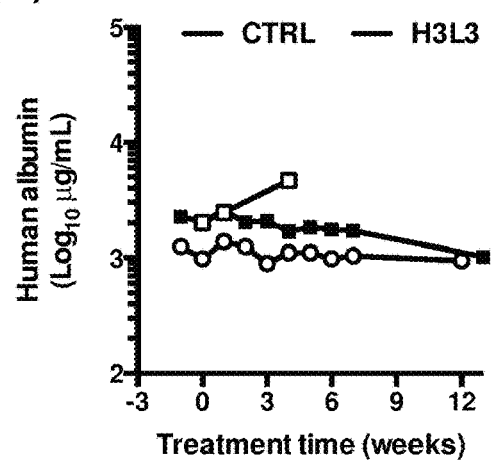
(C)
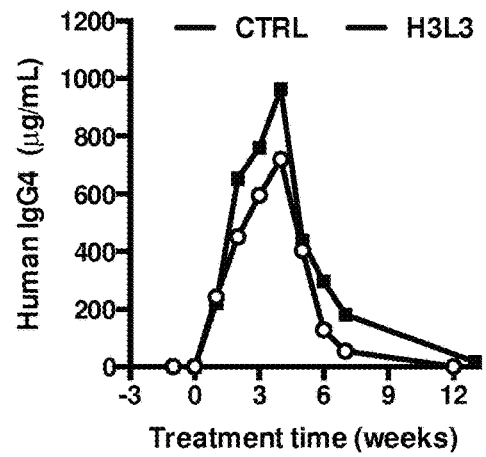
Figure 5

SEQUENCE LISTING

```
<160> NUMBER OF SEQ ID NOS: 12

<210> SEQ ID NO 1
<211> LENGTH: 119
<212> TYPE: PRT
<213> ORGANISM: Artificial Sequence
<220> FEATURE:
<223> OTHER INFORMATION: Humanized H3

<400> SEQUENCE: 1

Gln Val Gln Leu Val Glu Ser Gly Gly Gly Val Val Gln Pro Gly Arg
1               5                   10                  15

Ser Leu Arg Leu Ser Cys Leu Gly Ser Gly Phe Ser Phe Ser Ser Tyr
            20                  25                  30

Gly Met Asn Trp Val Arg Gln Ala Pro Gly Lys Gly Leu Glu Trp Val
        35                  40                  45

Ala Ser Ile Ser Pro Ser Gly Ser Tyr Phe Tyr Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Thr Ser Leu Arg Ala Glu Asp Thr Ala Ile Tyr Tyr Cys
                 85                  90                  95

Ala Arg Leu Pro Gly Phe Asn Pro Pro Phe Asp His Trp Gly Gln Gly
            100                 105                 110

Thr Leu Val Thr Val Ser Ser
            115

<210> SEQ ID NO 2
<211> LENGTH: 107
<212> TYPE: PRT
<213> ORGANISM: Artificial Sequence
<220> FEATURE:
<223> OTHER INFORMATION: humanized L3

<400> SEQUENCE: 2

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asn Val Gly Gly Asn
                 20                  25                  30

Val Asp Trp Tyr Gln Trp Lys Pro Gly Lys Ala Pro Lys Leu Leu Ile
             35                  40                  45

Tyr Gly Ala Ser Asn Arg Tyr Thr Gly Val Pro Asp Arg Phe Arg Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Leu Gln Tyr Lys Asn Asn Pro Trp
                 85                  90                  95

Thr Phe Gly Gly Gly Thr Lys Val Glu Ile Lys
            100                 105

<210> SEQ ID NO 3
<211> LENGTH: 119
<212> TYPE: PRT
<213> ORGANISM: Rattus norvegicus

<400> SEQUENCE: 3

Glu Val Gln Leu Val Glu Ser Gly Gly Leu Val Gln Pro Gly Arg
 1               5                  10                  15

Ser Leu Lys Leu Ser Cys Leu Gly Ser Gly Phe Ser Phe Ser Ser Tyr
                 20                  25                  30

Gly Met Asn Trp Ile Arg Gln Ala Pro Gly Lys Gly Leu Glu Trp Val
             35                  40                  45

Ala Ser Ile Ser Pro Ser Gly Ser Tyr Phe Tyr Tyr Ala Asp Ser Val
 50                  55                  60

Lys Gly Arg Phe Thr Ile Ser Arg Glu Asn Ala Lys Asn Thr Leu Tyr
 65                  70                  75                  80

Leu Gln Met Thr Ser Leu Arg Ala Glu Asp Thr Ala Leu Tyr Tyr Cys
                 85                  90                  95

Ala Arg Leu Pro Gly Phe Asn Pro Pro Phe Asp His Trp Gly Gln Gly
            100                 105                 110

Val Val Val Thr Val Ser Ser
            115

<210> SEQ ID NO 4
<211> LENGTH: 107
<212> TYPE: PRT
```

<213> ORGANISM: Rattus norvegicus

<400> SEQUENCE: 4

Asn Thr Val Met Thr Gln Ser Pro Thr Ser Met Phe Met Ser Val Gly
1               5                   10                  15

Asp Arg Val Thr Met Asn Cys Lys Ala Ser Gln Asn Val Gly Gly Asn
            20                  25                  30

Val Asp Trp Tyr Gln Trp Lys Pro Gly Gln Ser Pro Lys Leu Leu Met
        35                  40                  45

Tyr Gly Ala Ser Asn Arg Tyr Thr Gly Val Pro Asp Arg Phe Arg Gly
    50                  55                  60

Ser Gly Ser Gly Thr Asp Phe Thr Leu Thr Ile Ser Asn Met Gln Thr
65                  70                  75                  80

Glu Asp Leu Ala Val Tyr Tyr Cys Leu Gln Tyr Lys Asn Asn Pro Trp
                85                  90                  95

Thr Phe Gly Gly Gly Thr Lys Val Glu Leu Lys
            100                 105

<210> SEQ ID NO 5
<211> LENGTH: 113
<212> TYPE: PRT
<213> ORGANISM: Rattus norvegicus

<400> SEQUENCE: 5

Glu Val Gln Leu Val Glu Ser Gly Gly Gly Leu Val Gln Pro Gly Arg
1               5                   10                  15

Ser Leu Lys Leu Ser Cys Val Ala Ser Gly Phe Thr Phe Ser Asp Tyr
            20                  25                  30

Arg Met Asn Trp Ile Arg Gln Ala Pro Gly Lys Gly Leu Glu Trp Val
        35                  40                  45

Ala Ser Ile Ser Ser Ser Ser Tyr Ile Tyr Tyr Ala Asp Thr Val
    50                  55                  60

Lys Gly Phe Thr Ile Ser Arg Asp Asn Ala Lys Asp Thr Leu Tyr Leu
65                  70                  75                  80

Gln Met Thr Ser Leu Arg Ser Glu Asp Thr Ala Leu Tyr Tyr Cys Ala
                85                  90                  95

Arg Asp Tyr Phe Asp Tyr Trp Gly Gln Gly Val Met Val Thr Val Ser
            100                 105                 110

Ser

<210> SEQ ID NO 6
<211> LENGTH: 107
<212> TYPE: PRT
<213> ORGANISM: Rattus norvegicus

<400> SEQUENCE: 6

Asn Thr Val Met Thr Gln Ser Pro Thr Ser Met Phe Ile Ser Val Gly
1               5                   10                  15

Asp Arg Val Thr Met Asn Cys Lys Ala Ser Gln Asn Val Gly Thr Asn
            20                  25                  30

Val Asp Trp Tyr Gln Gln Lys Thr Gly Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Gly Thr Asp Phe Thr Leu Thr Ile Ser Asn Met Gln Ala
65                  70                  75                  80

Glu Asp Leu Ala Val Tyr Tyr Cys Leu Gln Tyr Asn Tyr Asn Pro Trp
                85                  90                  95

Thr Phe Gly Gly Gly Thr Lys Leu Glu Leu Lys
            100                 105

<210> SEQ ID NO 7
<211> LENGTH: 114
<212> TYPE: PRT
<213> ORGANISM: Homo sapiens

<400> SEQUENCE: 7

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Phe Asp Val Trp Gly Gln Gly Thr Met Val Thr Val
            100                 105                 110

Ser Ser

<210> SEQ ID NO 8
<211> LENGTH: 107
<212> TYPE: PRT
<213> ORGANISM: Homo sapiens

<400> SEQUENCE: 8

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Trp
                85                  90                  95

Thr Phe Gly Gln Gly Thr Lys Val Glu Ile Lys
            100                 105

<210> SEQ ID NO 9
<211> LENGTH: 119
<212> TYPE: PRT
<213> ORGANISM: Artificial Sequence
<220> FEATURE:
<223> OTHER INFORMATION: Humanized H1

<400> SEQUENCE: 9

Glu Val Gln Leu Val Glu Ser Gly Gly Gly Leu Val Lys Pro Gly Gly
1               5                   10                  15

```
Ser Leu Arg Leu Ser Cys Ala Ala Ser Gly Phe Ser Phe Ser Ser Tyr
            20                  25                  30

Gly Met Asn Trp Val Arg Gln Ala Pro Gly Lys Gly Leu Glu Trp Val
        35                  40                  45

Ser Ser Ile Ser Pro Ser Gly Ser Tyr Phe Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Leu Pro Gly Phe Asn Pro Pro Phe Asp His Trp Gly Gln Gly
            100                 105                 110

Thr Leu Val Thr Val Ser Ser
            115
```

<210> SEQ ID NO 10
<211> LENGTH: 107
<212> TYPE: PRT
<213> ORGANISM: Artificial Sequence
<220> FEATURE:
<223> OTHER INFORMATION: humanized L1

<400> SEQUENCE: 10

```
Asp Ile Gln Met Thr Gln Ser Pro Ala Thr Leu Ser Val Ser Pro Gly
 1               5                   10                  15

Glu Arg Ala Thr Leu Ser Cys Lys Ala Ser Gln Asn Val Gly Gly Asn
            20                  25                  30

Val Asp Trp Tyr Gln Trp Lys Pro Gly Gln Ala Pro Arg Leu Leu Ile
        35                  40                  45

Tyr Gly Ala Ser Asn Arg Tyr Thr Gly Ile Pro Ala Arg Phe Arg Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Leu Gln Tyr Lys Asn Asn Pro Trp
                85                  90                  95

Thr Phe Gly Gln Gly Thr Lys Val Glu Ile Lys
            100                 105
```

<210> SEQ ID NO 11
<211> LENGTH: 119
<212> TYPE: PRT
<213> ORGANISM: Artificial Sequence
<220> FEATURE:
<223> OTHER INFORMATION: humanized H2

<400> SEQUENCE: 11

```
Gln Val Gln Leu Val Glu Ser Gly Gly Gly Val Val Gln Pro Gly Arg
 1               5                   10                  15

Ser Leu Arg Leu Ser Cys Ala Ala Ser Gly Phe Ser Phe Ser Ser Tyr
            20                  25                  30

Gly Met Asn Trp Val Arg Gln Ala Pro Gly Lys Gly Leu Glu Trp Val
        35                  40                  45

Thr Ser Ile Ser Pro Ser Gly Ser Tyr Phe Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Ile Tyr Tyr Cys
                85                  90                  95
```

```
Ala Arg Leu Pro Gly Phe Asn Pro Pro Phe Asp His Trp Gly Gln Gly
            100                 105                 110

Thr Leu Val Thr Val Ser Ser
        115

<210> SEQ ID NO 12
<211> LENGTH: 107
<212> TYPE: PRT
<213> ORGANISM: Artificial Sequence
<220> FEATURE:
<223> OTHER INFORMATION: humanized L2

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Gly Asn
            20                  25                  30

Val Asp Trp Tyr Gln Trp Lys Pro Gly Lys Ala Pro Lys Leu Leu Ile
        35                  40                  45

Tyr Gly Ala Ser Asn Arg Tyr Thr Gly Val Pro Ser Arg Phe Arg Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gln Tyr Lys Asn Asn Pro Trp
                85                  90                  95

Thr Phe Gly Gln Gly Thr Lys Val Glu Ile Lys
            100                 105
```

HUMANIZED ANTI-CLAUDIN-1 ANTIBODIES AND USES THEREOF

SEQUENCE LISTING SUBMISSION VIA EFS-WEB

A computer readable text file, entitled "SequenceListing.txt" created on or about Sep. 20, 2018 with a file size of about 13 kb contains the sequence listing for this application and is hereby incorporated by reference in its entirety.

FIELD OF THE INVENTION

The present invention relates to humanized anti-claudin-1 antibodies and uses thereof, in particular for the prevention and treatment of hepatitis C virus infection, virus-associated liver disease and hepatocellular carcinoma.

BACKGROUND OF THE INVENTION

Chronic hepatitis C virus (HCV) infection is a leading cause of liver cirrhosis and hepatocellular carcinoma (HCC) worldwide. Although the recent approval of new classes of direct-acting antivirals (DAAs) has revolutionized HCV treatment, not all patient groups respond to therapy. In particular, genotype 3 HCV responds poorly to DAAs and is associated with steatosis and rapid progression to advanced liver disease (1). Treatment failure can also result from the selection of DAA-resistant HCV variants, as the targets of current DAAs are encoded by highly mutable viral genomes. The ability of DAAs to prevent liver graft reinfection remains to be determined (4). Furthermore, the extremely high costs of DAAs preclude access to therapy for the majority of patients, particularly in developing countries but also in high-resource settings.

Host-targeting agents (HTAs) offer an attractive complementary approach for antiviral therapies. In this context, HCV entry—a complex and highly orchestrated process—offers a number of antiviral targets, with the distinct advantage that HTAs blocking entry could prevent liver graft reinfection. Furthermore, as the targets of these molecules are encoded by the host cell genome, there is a higher genetic barrier to resistance. HCV requires several host factors to establish infection, including cluster of differentiation 81 (CD81) (5), scavenger receptor BI (SR-BI) (6), claudin-1 (CLDN1) (7), occludin (8), receptor tyrosine kinases (9), Niemann-Pick C1 Like 1 (NPC1L1) (10), Harvey rat sarcoma viral oncogene homolog (HRas) (11), and transferrin receptor 1 (12). As these host factors are essential for HCV entry and contribute to persistence, they are also attractive targets for the development of broad and potent anti-HCV agents. Indeed, antibodies targeting CD81 (13-16), SR-B1 (17-19) and CLDN1 (20, 21) have been shown to potently and pan-genotypically inhibit HCV infection in vitro and in vivo, and small molecules targeting EGFR (9), NPC1L1 (10) and HRas (11) similarly exhibit anti-HCV activities. Importantly, HTAs act synergistically with DAAs (22) and have been shown to prevent emergence of DAA-resistant variants (23), which are attractive features for use in combination therapy.

The inventors previously reported the production of rat anti-CLDN1 monoclonal antibodies (mAbs) with robust anti-HCV activities in vitro (20, 24 and WO2010034812) using HCV pseudoparticle (HCVpp) and cell culture-derived HCV (HCVcc) model systems, with hepatoma cells and primary human hepatocytes (PHH). These antibodies inhibited HCV entry by disrupting formation of the CD81-CLDN1 co-receptor complex. Furthermore, they recently reported that the lead rat anti-CLDN1 mAb (OM-7D3-B3) prevents de novo HCV infection and clears chronic HCV infection without inducing any toxicity in human-liver chimeric uPA SCID mice (21). Given these most promising findings, humanization of this antibody represents the next step in its clinical development.

SUMMARY OF THE INVENTION

The present invention relates to humanized anti-claudin-1 antibodies and uses thereof, in particular for the treatment of hepatitis C virus infection. In particular, the present invention is defined by the claims.

DETAILED DESCRIPTION OF THE INVENTION

Hepatitis C virus infection is a leading cause of chronic liver disease and a major indication for liver transplantation. Although direct-acting antivirals (DAAs) efficiently cure chronic HCV infection, alternative strategies are still needed for patients with treatment failure. Furthermore, the ability of DAAs to prevent liver graft reinfection is still under clinical investigation. Host-targeting agents are attractive alternatives to DAAs due to their pan-genotypic effects and high genetic barrier to resistance. The tight junction protein claudin-1 (CLDN1) is an essential entry factor for HCV and a promising target for therapy. The inventors recently described a rat anti-CLDN1 antibody produced by genetic immunization that could not only prevent HCV infection but also cure chronically infected human liver chimeric mice. To further its clinical development, the inventors have now humanized this antibody. The lead humanized anti-CLDN1 antibody (H3L3) pan-genotypically inhibited HCV pseudoparticle infection of primary human hepatocytes (PHH) without detectable escape, likely due to low expression levels of other claudin subtypes in PHH. H3L3 efficiently inhibited infection by diverse HCV genotype 3 strains and exhibited marked synergy with DAAs. Finally, the inventors demonstrate that anti-CLDN1 H3L3 cures persistent HCV infection in human-liver chimeric uPA-SCID mice in monotherapy. This study paves the way for pre-clinical and clinical studies aimed at further development of anti-CLDN1 antibodies for the prevention and cure of HCV infection.

A first aspect of the present invention thus provides anti-claudin-1 humanized antibodies.

As used herein, the term "Claudin-1" or "CLDN1" has its general meaning in the art and refers to the integral membrane protein associated with tight junction claudin-1. The CLDN1 has been first identified as a 22-kD polypeptide from isolated chicken liver junction fractions and cDNAs encoding their mouse homologues were cloned (Furuse et al., 1998). Human cDNA of CLDN1 (alias=SEMP1) was cloned and sequenced (Swisshelm et al., 1999). It contains four exons including 636 nucleotides. The translation gives a product of 211 amino acid residues. CLDN1 has a tetraspan membrane topology with four transmembrane regions. Intracellularly, CLDN1 exhibits a 7 amino-acids N-terminus, a 12 amino acid loop and a 27 amino-acid C-terminus. The extracellular loop (ECL) 1 consists of 53 amino acids with two conserved cysteines. The ECL2 has 27 amino acids, The term "human Claudin-1 or human CLDN1" refers to a protein having the sequence shown in NCBI Accession Number NP_066924, or any naturally occurring variants. The term "extracellular domain" or "ectodomain" of Claudin-1 refers to the region of the Claudin-1 sequence that extends into the extracellular space (i.e., the space outside a cell).

As used herein the term "antibody" or "immunoglobulin" have the same meaning, and will be used equally in the present invention. The term "antibody" as used herein refers to immunoglobulin molecules and immunologically active portions of immunoglobulin molecules, i.e., molecules that contain an antigen binding site that immunospecifically binds an antigen. As such, the term antibody encompasses not only whole antibody molecules, but also antibody fragments as well as variants (including derivatives) of antibodies and antibody fragments. In natural antibodies, two heavy chains are linked to each other by disulfide bonds and each heavy chain is linked to a light chain by a disulfide bond. There are two types of light chain, lambda (l) and kappa (k). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CHI, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, trans-placental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) can participate to the antibody binding site or influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, typically includes six CDRs, comprising the CDR set from each of a heavy and a light chain V region. Framework Regions (FRs) refer to amino acid sequences interposed between CDRs. The residues in antibody variable domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al."). This numbering system is used in the present specification. The Kabat residue designations do not always correspond directly with the linear numbering of the amino acid residues in SEQ ID sequences. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence. The CDRs of the heavy chain variable domain are located at residues 31-35B (H-CDR1), residues 50-65 (H-CDR2) and residues 95-102 (H-CDR3) according to the Kabat numbering system. The CDRs of the light chain variable domain are located at residues 24-34 (L-CDR1), residues 50-56 (L-CDR2) and residues 89-97 (L-CDR3) according to the Kabat numbering system.

As used herein the term "humanized antibody" refers to a chimeric antibody comprising amino acid residues from non-human hypervariable regions and amino acid residues from human FRs. In particular, a humanized antibody will comprise substantially all of at least one, and typically two, variable domains, in which all or substantially all of the CDRs correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

Accordingly a first aspect of the present invention relates to a humanized antibody comprising a) at least one antibody variable heavy chain (VH) consisting of the amino acid sequence of SEQ ID NO:1, or b) at least one antibody variable light chain (VL) consisting of the amino acid sequence of SEQ ID NO:2, or c) at least one antibody variable heavy chain (VH) consisting of the amino acid sequence of SEQ ID NO:1, and at least one antibody variable light chain (VL) consisting of the amino acid sequence of SEQ ID NO:2.

```
SEQ ID NO: 1: humanized variable heavy chain H3
QVQLVESGGGVVQPGRSLRLSCLGSGFSFSSYGMNWVRQAPGKGLEWVA
SISPSGSYFYYADSVKGRFTISRDNSKNTLYLQMTSLRAEDTAIYYCARL
PGFNPPFDHWGQGTLVTVSS SEQ ID NO: 2: humanized variable light chain L3
DIQMTQSPSSLSASVGDRVTITCKASQNVGGNVDWYQWKPGKAPKLLIYG
ASNRYTGVPDRFRGSGSGTDFTLTISSLQPEDVATYYCLQYKNNPWTFGG
GTKVEIK
```

In some embodiments, the humanized antibody of the present invention comprises a) two antibody variable heavy chains (VH) consisting of the amino acid sequence of SEQ ID NO:1 or b) two antibody variable light chains (VL) consisting of the amino acid sequence of SEQ ID NO:2 or, c) two antibody variable heavy chains (VH) consisting of the amino acid sequence of SEQ ID NO:1 and two antibody variable light chains (VL) consisting of the amino acid sequence of SEQ ID NO:2.

According to the invention, the humanized antibody of the present invention is a monoclonal antibody. The terms "monoclonal antibody", "monoclonal Ab", "monoclonal antibody composition", "mAb", or the like, as used herein refer to a preparation of antibody molecules of single molecular composition. A monoclonal antibody composition displays a single binding specificity and affinity for a particular epitope.

The humanized antibody of the present invention can be characterized by one or more of the functional or structural features of the aspects described above, or by any combination of selected functional and structural features.

The humanized antibody of the present invention may be of any isotype. The choice of isotype typically will be guided by the desired effector functions, such as ADCC induction. Exemplary isotypes are IgG1, IgG2, IgG3, and IgG4. Either of the human light chain constant regions, kappa or lambda, may be used. If desired, the class of a humanized antibody of the present invention may be switched by known methods. Typical, class switching techniques may be used to convert one IgG subclass to another, for instance from IgG1 to IgG2. Thus, the effector function of the humanized antibodies of the present invention may be changed by isotype switching to, e.g., an IgG1, IgG2, IgG3, IgG4, IgD, IgA, IgE, or IgM antibody for various therapeutic uses. In some embodiments, the humanized antibody of the present invention is a full-length antibody. In some embodiments, the full-length antibody is an IgG1 antibody. In some embodiments, the full-length antibody is an IgG4 antibody. In some embodiments, the CLDN1-specific IgG4 antibody is a stabilized IgG4 antibody. Examples of suitable stabilized IgG4 antibodies are antibodies wherein arginine at position 409 in a heavy chain constant region of human IgG4, which is indicated in the EU index as in Kabat et al. supra, is substituted with lysine, threonine, methionine, or leucine, preferably lysine (described in WO2006033386) and/or wherein the hinge region comprises a Cys-Pro-Pro-Cys sequence. Other suitable stabilized IgG4 antibodies are disclosed in WO2008145142, which is hereby incorporated by reference in its entirety. In some embodiments, the humanized antibody of the present invention is an antibody of a non-IgG4 type, e.g. IgG1, IgG2 or IgG3 which has been mutated such that the ability to mediate effector functions, such as ADCC, has been reduced or even eliminated. Such mutations have e.g. been described in Dall'Acqua W F et al., J Immunol. 177(2): 1129-1138 (2006) and Hezareh M, J Virol. 75(24): 12161-12168 (2001).

In some embodiments, modifications made within the framework or CDR regions may be engineered to alter one or more functional properties of the antibody. For example, it will be appreciated that the affinity of antibodies provided by the present invention may be altered using any suitable method known in the art. The present invention therefore also relates to variants of the antibody molecules of the present invention, which have an improved affinity for CLDN1. Numerous methods for affinity maturation of antibodies are known in the art including mutating the CDRs (Yang et al., J. Mol. Biol., 254, 392-403, 1995), chain shuffling (Marks et al., Bio/Technology, 10, 779-783, 1992), use of mutator strains of E. coli (Low et al., J. Mol. Biol., 250, 359-368, 1996), DNA shuffling (Patten et al., Curr. Opin. Biotechnol., 8, 724-733, 1997), phage display (Thompson et al., J. Mol. Biol., 256, 77-88, 1996) and PCR (Crameri et al., Nature, 391, 288-291, 1998). For instance, phage display technology can be used to increase the affinity of the disclosed antibodies. This technique would be useful in obtaining high affinity antibodies that could be used in the combinatorial methods. This technology, referred to as affinity maturation, employs mutagenesis or CDR walking and re-selection using such receptors or ligands (or their extracellular domains) or an antigenic fragment thereof to identify antibodies that bind with higher affinity to the antigen when compared with the initial or parental antibody (See, e.g., Glaser, S. M. et al. (1992) "Antibody Engineering By Codon-Based Mutagenesis In A Filamentous Phage Vector System," J. Immunol. 149:3903-3913). Mutagenizing entire codons rather than single nucleotides results in a semi-randomized repertoire of amino acid mutations. Libraries can be constructed consisting of a pool of variant clones each of which differs by a single amino acid alteration in a single CDR and which contain variants representing each possible amino acid substitution for each CDR residue. Mutants with increased binding affinity for the antigen can be screened by contacting the immobilized mutants with labeled antigen. Any screening method known in the art can be used to identify mutant antibodies with increased avidity to the antigen (e.g., ELISA) (see, e.g., Wu, H. et al. (1998) "Stepwise In Vitro Affinity Maturation Of Vitaxin, An Alphav Beta3-Specific Humanized Mab," Proc. Natl. Acad. Sci. (USA) 95(11):6037-6042; Yelton, D. E. et al. (1995) "Affinity Maturation Of The BR96 Anti-Carcinoma Antibody By Codon-Based Mutagenesis," J. Immunol. 155: 1994-2004). CDR walking which randomizes the light chain may be used possible (see, Schier et al. (1996) "Isolation Of Picomolar Affinity Anti-C-Erbb-2 Single-Chain Fv By Molecular Evolution Of The Complementarity Determining Regions In The Center Of The Antibody Binding Site," J. Mol. Biol. 263:551-567). Random mutagenesis can also be used to identify improved CDRs. Phage display technology can alternatively be used to increase (or decrease) CDR affinity. This technology, referred to as affinity maturation, employs mutagenesis or "CDR walking" and re-selection uses the target antigen or an antigenic fragment thereof to identify antibodies having CDRs that bind with higher (or lower) affinity to the antigen when compared with the initial or parental antibody (see, e.g., Glaser, S. M. et al. (1992) "Antibody Engineering By Codon-Based Mutagenesis In A Filamentous Phage Vector System," J. Immunol. 149:3903-3913). Mutagenizing entire codons rather than single nucleotides results in a semi-randomized repertoire of amino acid mutations. Libraries can be constructed consisting of a pool of variant clones each of which differs by a single amino acid alteration in a single CDR and which contain variants representing each possible amino acid substitution for each CDR residue. Mutants with increased (or decreased) binding affinity for the antigen can be screened by contacting the immobilized mutants with labeled antigen. Any screening method known in the art can be used to identify mutant antibodies with increased (or decreased) avidity to the antigen (e.g., ELISA) (see, Wu, H. et al. (1998) "Stepwise In Vitro Affinity Maturation Of Vitaxin, An Alphav Beta3-Specific Humanized Mab," Proc. Natl. Acad. Sci. (USA) 95(11):6037-6042; Yelton, D. E. et al. (1995) "Affinity Maturation Of The BR96 Anti-Carcinoma Antibody By Codon-Based Mutagenesis," J. Immunol. 155: 1994-2004). CDR walking which randomizes the light chain may be used possible (see, Schier et al. (1996) "Isolation Of Picomolar Affinity Anti-C-Erbb-2 Single-Chain Fv By Molecular Evolution Of The Complementarity Determining Regions In The Center Of The Antibody Binding Site," J. Mol. Biol. 263:551-567). Methods for accomplishing such affinity maturation are described for example in: Krause, J. C. et al. (2011) "An Insertion Mutation That Distorts Antibody Binding Site Architecture Enhances Function Of A Human Antibody," M Bio. 2(1) pii: e00345-10. doi: 10.1128/mBio.00345-10; Kuan, C. T. et al. (2010) "Affinity-Matured Anti-Glycoprotein NMB Recombinant Immunotoxins Targeting Malignant Gliomas And Melanomas," Int. J. Cancer 10.1002/ijc.25645; Hackel, B. J. et al. (2010) "Stability And CDR Composition Biases Enrich Binder Functionality Landscapes," J. Mol. Biol. 401(1):84-96; Montgomery, D. L. et al. (2009) "Affinity Maturation And Characterization Of A Human Monoclonal Antibody Against HIV-1 gp41," MAbs 1(5):462-474; Gustchina, E. et al. (2009) "Affinity Maturation By Targeted Diversification Of The CDR-H2 Loop Of A Monoclonal Fab Derived From A Synthetic Naïve Human Antibody Library And Directed Against The Internal Trimeric Coiled-Coil Of Gp41 Yields A Set Of Fabs With Improved HIV-1 Neutralization Potency And Breadth," Virology 393(1):112-119; Finlay, W. J. et al. (2009) "Affinity Maturation Of A Humanized Rat Antibody For Anti-RAGE Therapy: Comprehensive Mutagenesis Reveals A High Level Of Mutational Plasticity Both Inside And Outside The Complementarity-Determining Regions," J. Mol. Biol. 388(3):541-558; Bostrom, J. et al. (2009) "Improving Antibody Binding Affinity And Specificity For Therapeutic Development," Methods Mol. Biol. 525:353-376; Steidl, S. et al. (2008) "In Vitro Affinity Maturation Of Human GM-CSF Antibodies By Targeted CDR-Diversification," Mol. Immunol. 46(1):135-144; and Barderas, R. et al. (2008) "Affinity maturation of antibodies assisted by in silico modeling," Proc. Natl. Acad. Sci. (USA) 105(26): 9029-9034.

In some embodiments, the humanized antibody of the present invention may be engineered to include modifications within the Fc region, typically to alter one or more functional properties of the antibody, such as serum half-life, complement fixation, Fc receptor binding, and/or antigen-dependent cellular cytotoxicity. Furthermore, a humanized antibody of the present invention may be chemically modified (e.g., one or more chemical moieties can be attached to the antibody) or be modified to alter its glycosylation, again to alter one or more functional properties of the antibody.

In some embodiments, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In some embodiments, the humanized antibody of the present invention is modified to increase its biological half-life. Various approaches are possible. For example, one or more of the following mutations can be introduced: T252L, T254S, T256F, as described in U.S. Pat. No. 6,277, 375 by Ward. Alternatively, to increase the biological half-life, the antibody can be altered within the CHI or CL region to contain a salvage receptor binding epitope taken from two loops of a CH2 domain of an Fc region of an IgG, as described in U.S. Pat. Nos. 5,869,046 and 6,121,022 by Presta et al.

In some embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the CI component of complement. This approach is described in further detail in U.S. Pat. Nos. 5,624,821 and 5,648,260, both by Winter et al.

In some embodiments, one or more amino acids selected from amino acid residues can be replaced with a different amino acid residue such that the antibody has altered C1q binding and/or reduced or abolished complement dependent cytotoxicity (CDC). This approach is described in further detail in U.S. Pat. No. 6,194,551 by ldusogie et al.

In some embodiments, one or more amino acid residues are altered to thereby alter the ability of the antibody to fix complement. This approach is described further in PCT Publication WO 94/29351 by Bodmer et al. In some embodiments, the Fc region is modified to increase the ability of the antibody to mediate antibody dependent cellular cytotoxicity (ADCC) and/or to increase the affinity of the antibody for an Fc receptor by modifying one or more amino acids. This approach is described further in PCT Publication WO 00/42072 by Presta. Moreover, the binding sites on human IgGI for FcyRI, FcyRII, FcyRIII and FcRn have been mapped and variants with improved binding have been described (see Shields, R. L. et al, 2001 J. Biol. Chen. 276:6591-6604, WO2010106180).

In some embodiments, the glycosylation of the antibody is modified. For example, an aglycosylated antibody can be made (i.e., the antibody lacks glycosylation). Glycosylation can be altered to, for example, increase the affinity of the antibody for the antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al. Additionally or alternatively, an antibody can be made that has an altered type of glycosylation, such as a hypofucosylated or non-fucosylated antibody having reduced amounts of or no fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the present invention to thereby produce an antibody with altered glycosylation. For example, EP1,176,195 by Hang et al. describes a cell line with a functionally disrupted FUT8 gene, which encodes a fucosyl transferase, such that antibodies expressed in such a cell line exhibit hypofucosylation or are devoid of fucosyl residues. Therefore, in some embodiments, the humanized antibodies of the present invention may be produced by recombinant expression in a cell line which exhibit hypofucosylation or non-fucosylation pattern, for example, a mammalian cell line with deficient expression of the FUT8 gene encoding fucosyltransferase. PCT Publication WO 03/035835 by Presta describes a variant CHO cell line, Lecl3 cells, with reduced ability to attach fucose to Asn(297)-linked carbohydrates, also resulting in hypofucosylation of antibodies expressed in that host cell (see also Shields, R. L. et al, 2002 J. Biol. Chem. 277:26733-26740). PCT Publication WO 99/54342 by Umana et al. describes cell lines engineered to express glycoprotein-modifying glycosyl transferases (e.g., beta(1, 4)-N acetylglucosaminyltransferase III (GnTIII)) such that antibodies expressed in the engineered cell lines exhibit increased bisecting GlcNac structures which results in increased ADCC activity of the antibodies (see also Umana et al, 1999 Nat. Biotech. 17: 176-180). Eureka Therapeutics further describes genetically engineered CHO mammalian cells capable of producing antibodies with altered mammalian glycosylation pattern devoid of fucosyl residues (http://www.eurekainc.com/a&boutus/companyoverview.html). Alternatively, the humanized antibodies of the present invention can be produced in yeasts or filamentous fungi engineered for mammalian-like glycosylation pattern and capable of producing antibodies lacking fucose as glycosylation pattern (see for example EP1297172B1).

Another modification of the humanized antibody of the present invention herein that is contemplated by the present invention is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (CI-CIO) alkoxy- or aryloxy-poly ethylene glycol or polyethylene glycol-maleimide. In some embodiments, the antibody to be pegylated is an aglycosylated antibody. Methods for pegylating proteins are known in the art and can be applied to the humanized antibodies of the present invention. See for example, EP0154316 by Nishimura et al. and EP0401384 by Ishikawa et al.

Another modification of the humanized antibody that is contemplated by the present invention is a conjugate or a protein fusion of at least the antigen-binding region of the humanized antibody of the present invention to serum protein, such as human serum albumin or a fragment thereof to increase half-life of the resulting molecule. Such approach is for example described in Ballance et al. EP0322094.

In some embodiments, the humanized antibody of the present invention is an antigen-binding fragment. Antibody fragments can be obtained by conventional techniques, such as by fragmentation of full-length antibodies or by expression of nucleic acids encoding antibody fragments in recombinant cells (see, for instance Evans et al., J. Immunol. Meth. 184, 123-38 (1995)). The fragments can then be tested or screened for their properties in the same manner as described herein for full-length antibodies. The following describe exemplary formats for CLDN1-specific antigen-binding fragments of the present invention:

F(ab')2 fragments, which are bivalent fragments comprising two Fab fragments linked by a disulfide bridge at the hinge region. These can be generated by, e.g., treating a full-length antibody with pepsin.

Fab' or Fab fragments, which are monovalent fragments consisting of the VL, VH, CL and CH1 domains. Fab fragments can be obtained, e.g., by treating an IgG antibody with papain. Fab' fragments can be obtained, e.g., by reducing the disulfide bridges of a F(ab')2 fragment using a reducing agent such as dithiothreitol.

Fd fragments, which consist essentially of the VH and CH1 domains.

Fv fragments, which consist essentially of the VL and VH domains of a single arm of an antibody and single-chain antibodies thereof. Single-chain antibodies (also known as single chain Fv (scFv) antibodies) are constructs where the VL and VH domains of an Fv fragment are joined, using recombinant methods, by a synthetic linker that enables them to be expressed as a single protein chain in which the VL and VH regions pair to form monovalent molecules (see for instance Bird et a/., Science 242, 423-426 (1988) and Huston et al., PNAS USA 85, 5879-5883 (1988)).

In some embodiments, the present invention provides a multispecific antibody comprising at least one variable heavy or light chain from a humanized antibody of the present invention molecule described herein above and at least one second antigen binding site. In some embodiments, the second antigen-binding site is used for recruiting a killing mechanism such as, for example, by binding an antigen on a human effector cell or by binding a cytotoxic agent or a second therapeutic agent. As used herein, the term "effector cell" refers to an immune cell which is involved in the effector phase of an immune response, as opposed to the cognitive and activation phases of an immune response. Exemplary immune cells include a cell of a myeloid or lymphoid origin, for instance lymphocytes (such as B cells and T cells including cytolytic T cells (CTLs)), killer cells, natural killer cells, macrophages, monocytes, mast cells and granulocytes, such as neutrophils, eosinophils and basophils. Some effector cells express specific Fc receptors (FcRs) and carry out specific immune functions. In some embodiments, an effector cell is capable of inducing ADCC, such as a natural killer cell. For example, monocytes, macrophages, which express FcRs, are involved in specific killing of target cells and presenting antigens to other components of the immune system. In some embodiments, an effector cell may phagocytose a target antigen or target cell. The expression of a particular FcR on an effector cell may be regulated by humoral factors such as cytokines. An effector cell can phagocytose a target antigen or phagocytose or lyse a target cell. Suitable cytotoxic agents and second therapeutic agents are exemplified below, and include toxins (such as radiolabeled peptides), chemotherapeutic agents and prodrugs.

In some embodiments, the second antigen-binding site binds a tissue-specific antigen, promoting localization of the multispecific antibody to a specific tissue.

Exemplary formats for the multispecific antibody molecules of the present invention include, but are not limited to (i) two antibodies cross-linked by chemical heteroconjugation, one with a specificity to CLDN1 and another with a specificity to a second antigen; (ii) a single antibody that comprises two different antigen-binding regions; (iii) a single-chain antibody that comprises two different antigen-binding regions, e.g., two scFvs linked in tandem by an extra peptide linker; (iv) a dual-variable-domain antibody (DVD-Ig), where each light chain and heavy chain contains two variable domains in tandem through a short peptide linkage (Wu et al., Generation and Characterization of a Dual Variable Domain Immunoglobulin (DVD-Ig™) Molecule, In: Antibody Engineering, Springer Berlin Heidelberg (2010)); (v) a chemically-linked bispecific (Fab')2 fragment; (vi) a Tandab, which is a fusion of two single chain diabodies resulting in a tetravalent bispecific antibody that has two binding sites for each of the target antigens; (vii) a flexibody, which is a combination of scFvs with a diabody resulting in a multivalent molecule; (viii) a so called "dock and lock" molecule, based on the "dimerization and docking domain" in Protein Kinase A, which, when applied to Fabs, can yield a trivalent bispecific binding protein consisting of two identical Fab fragments linked to a different Fab fragment; (ix) a so-called Scorpion molecule, comprising, e.g., two scFvs fused to both termini of a human Fab-arm; and (x) a diabody. Another exemplary format for bispecific antibodies is IgG-like molecules with complementary CH3 domains to force heterodimerization. Such molecules can be prepared using known technologies, such as, e.g., those known as Triomab/Quadroma (Trion Pharma/Fresenius Biotech), Knob-into-Hole (Genentech), CrossMAb (Roche) and electrostatically-matched (Amgen), LUZ-Y (Genentech), Strand Exchange Engineered Domain body (SEEDbody) (EMD Serono), Biclonic (Merus) and DuoBody (Genmab A/S) technologies.

In some embodiments, the bispecific antibody is obtained or obtainable via a controlled Fab-arm exchange, typically using DuoBody technology. In vitro methods for producing bispecific antibodies by controlled Fab-arm exchange have been described in WO2008119353 and WO 2011131746 (both by Genmab A/S). In one exemplary method, described in WO 2008119353, a bispecific antibody is formed by "Fab-arm" or "half-molecule" exchange (swapping of a heavy chain and attached light chain) between two monospecific antibodies, both comprising IgG4-like CH3 regions, upon incubation under reducing conditions. The resulting product is a bispecific antibody having two Fab arms which may comprise different sequences. In another exemplary method, described in WO 2011131746, bispecific antibodies of the present invention are prepared by a method comprising the following steps, wherein at least one of the first and second antibodies is a humanized antibody of the present invention: a) providing a first antibody comprising an Fc region of an immunoglobulin, said Fc region comprising a first CH3 region; b) providing a second antibody comprising an Fc region of an immunoglobulin, said Fc region comprising a second CH3 region; wherein the sequences of said first and second CH3 regions are different and are such that the heterodimeric interaction between said first and second CH3 regions is stronger than each of the homodimeric interactions of said first and second CH3 regions; c) incubating said first antibody together with said second antibody under reducing conditions; and d) obtaining said bispecific antibody, wherein the first antibody is a humanized antibody of the present invention and the second antibody has a different binding specificity, or vice versa. The reducing conditions may, for example, be provided by adding a reducing agent, e.g. selected from 2-mercaptoethylamine, dithiothreitol and tris(2-carboxyethyl)phosphine. Step d) may further comprise restoring the conditions to become non-reducing or less reducing, for example by removal of a reducing agent, e.g. by desalting. Preferably, the sequences of the first and second CH3 regions are different, comprising only a few, fairly conservative, asymmetrical mutations, such that the heterodimeric interaction between said first and second CH3 regions is stronger than each of the homodimeric interactions of said first and second CH3 regions. More details on these interactions and how they can be achieved are provided in WO 2011131746, which is hereby incorporated by reference in its entirety. The following are exemplary embodiments of combinations of such assymetrical mutations, optionally wherein one or both Fc-regions are of the IgG1 isotype.

In some embodiments, the first Fc region has an amino acid substitution at a position selected from the group consisting of: 366, 368, 370, 399, 405, 407 and 409, and the second Fc region has an amino acid substitution at a position selected from the group consisting of: 366, 368, 370, 399, 405, 407 and 409, and wherein the first and second Fc regions are not substituted in the same positions.

In some embodiments, the first Fc region has an amino acid substitution at position 405, and said second Fc region has an amino acid substitution at a position selected from the group consisting of: 366, 368, 370, 399, 407 and 409, optionally 409.

In some embodiments, the first Fc region has an amino acid substitution at position 409, and said second Fc region has an amino acid substitution at a position selected from the group consisting of: 366, 368, 370, 399, 405, and 407, optionally 405 or 368.

In some embodiments, both the first and second Fc regions are of the IgG1 isotype, with the first Fc region having a Leu at position 405, and the second Fc region having an Arg at position 409.

The humanized antibody of the present invention may be produced by any technique known in the art, such as, without limitation, any chemical, biological, genetic or enzymatic technique, either alone or in combination. For example, knowing the amino acid sequence of the desired sequence, one skilled in the art can readily produce said antibodies, by standard techniques for production of polypeptides. For instance, they can be synthesized using well-known solid phase method, preferably using a commercially available peptide synthesis apparatus (such as that made by Applied Biosystems, Foster City, Calif.) and following the manufacturer's instructions. Alternatively, antibodies of the present invention can be synthesized by recombinant DNA techniques well-known in the art. For example, antibodies can be obtained as DNA expression products after incorporation of DNA sequences encoding the antibodies into expression vectors and introduction of such vectors into suitable eukaryotic or prokaryotic hosts that will express the desired antibodies, from which they can be later isolated using well-known techniques.

Accordingly, a further object of the present invention relates to a nucleic acid sequence encoding a humanized antibody of the present invention. In some embodiments, the nucleic acid sequence encodes a heavy chain and/or a light chain of a humanized antibody of the present invention.

Typically, said nucleic acid is a DNA or RNA molecule, which may be included in any suitable vector. The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (for instance bacterial vectors having a bacterial origin of replication and episomal mammalian vectors). Other vectors (such as non-episomal mammalian vectors) may be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the present invention is intended to include such other forms of expression vectors, such as viral vectors (such as replication-defective retroviruses, adenoviruses and adeno-associated viruses), which serve equivalent functions.

So, a further object of the present invention relates to a vector comprising a nucleic acid of the present invention.

Such vectors may comprise regulatory elements, such as a promoter, enhancer, terminator and the like, to cause or direct expression of said antibody upon administration to a subject. Examples of promoters and enhancers used in the expression vector for animal cell include early promoter and enhancer of SV40 (Mizukami T. et al. 1987), LTR promoter and enhancer of Moloney mouse leukemia virus (Kuwana Y et al. 1987), promoter (Mason J O et al. 1985) and enhancer (Gillies S D et al. 1983) of immunoglobulin H chain and the like. Any expression vector for animal cell can be used, so long as a gene encoding the human antibody C region can be inserted and expressed. Examples of suitable vectors include pAGE107 (Miyaji H et al. 1990), pAGE103 (Mizukami T et al. 1987), pHSG274 (Brady G et al. 1984), pKCR (O'Hare K et al. 1981), pSG1 beta d2-4-(Miyaji H et al. 1990) and the like. Other examples of plasmids include replicating plasmids comprising an origin of replication, or integrative plasmids, such as for instance pUC, pcDNA, pBR, and the like. Other examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. Nos. 5,882,877, 6,013,516, 4,861,719, 5,278,056 and WO 94/19478.

A further object of the present invention relates to a host cell which has been transfected, infected or transformed by a nucleic acid and/or a vector according to the present invention.

The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA has been "transformed».

The nucleic acids of the present invention may be used to produce a humanized antibody of the present invention in a suitable expression system. The term "expression system" means a host cell and compatible vector under suitable conditions, e.g. for the expression of a protein coded for by foreign DNA carried by the vector and introduced to the host cell. Common expression systems include *E. coli* host cells and plasmid vectors, insect host cells and Baculo virus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include *E. coli, Kluyveromyces* or *Saccharomyces* yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). Examples also include mouse SP2/0-Agl4 cell (ATCC CRL1581), mouse P3X63-Ag8.653 cell (ATCC CRL1580), CHO cell in which a dihydrofolate reductase gene (hereinafter referred to as "DHFR gene") is defective (Urlaub G et al; 1980), rat YB2/3HL.P2.G1 1.16Ag.20 cell (ATCC CRL1662, hereinafter referred to as "YB2/0 cell"), and the like.

The present invention also relates to a method of producing a recombinant host cell expressing an antibody according to the present invention, said method comprising the steps of: (i) introducing in vitro or ex vivo a recombinant nucleic acid or a vector as described above into a competent host cell, (ii) culturing in vitro or ex vivo the recombinant host cell obtained and (iii), optionally, selecting the cells which express and/or secrete said antibody. Such recombinant host cells can be used for the production of antibodies of the present invention.

In some embodiments, the humanized antibody of the present invention is conjugated to a therapeutic moiety, i.e. a drug. The therapeutic moiety can be, e.g., a cytotoxin, a chemotherapeutic agent, a cytokine, an immunosuppressant, an immune stimulator, a lytic peptide, or a radioisotope. Such conjugates are referred to herein as an "antibody-drug conjugates" or "ADCs".

In some embodiments, the antibody is conjugated to a cytotoxic moiety. The cytotoxic moiety may, for example, be selected from the group consisting of taxol; cytochalasin B; gramicidin D; ethidium bromide; emetine; mitomycin; etoposide; tenoposide; vincristine; vinblastine; colchicin; doxorubicin; daunorubicin; dihydroxy anthracin dione; a tubulin-inhibitor such as maytansine or an analog or derivative thereof; an antimitotic agent such as monomethyl auristatin E or F or an analog or derivative thereof; dolastatin 10 or 15 or an analogue thereof; irinotecan or an analogue thereof; mitoxantrone; mithramycin; actinomycin D; 1-dehydrotestosterone; a glucocorticoid; procaine; tetracaine; lidocaine; propranolol; puromycin; calicheamicin or an analog or derivative thereof; an antimetabolite such as methotrexate, 6 mercaptopurine, 6 thioguanine, cytarabine, fludarabin, 5 fluorouracil, decarbazine, hydroxyurea, asparaginase, gemcitabine, or cladribine; an alkylating agent such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C; a platinum derivative such as cisplatin or carboplatin; duocarmycin A, duocarmycin SA, rachelmycin (CC-1065), or an analog or derivative thereof; an antibiotic such as dactinomycin, bleomycin, daunorubicin, doxorubicin, idarubicin, mithramycin, mitomycin, mitoxantrone, plicamycin, anthramycin (AMC)); pyrrolo[2,1-c][1,4]-benzodiazepines (PDB); diphtheria toxin and related molecules such as diphtheria A chain and active fragments thereof and hybrid molecules, ricin toxin such as ricin A or a deglycosylated ricin A chain toxin, cholera toxin, a Shiga-like toxin such as SLT I, SLT II, SLT IIV, LT toxin, C3 toxin, Shiga toxin, pertussis toxin, tetanus toxin, soybean Bowman-Birk protease inhibitor, *Pseudomonas* exotoxin, alorin, saporin, modeccin, gelanin, abrin A chain, modeccin A chain, alpha-sarcin, *Aleurites fordii* proteins, dianthin proteins, *Phytolacca americana* proteins such as PAPI, PAPII, and PAP-S, *Momordica charantia* inhibitor, curcin, crotin, *Sapaonaria officinalis* inhibitor, gelonin, mitogellin, restrictocin, phenomycin, and enomycin toxins; ribonuclease (RNase); DNase I, Staphylococcal enterotoxin A; pokeweed antiviral protein; diphtherin toxin; and *Pseudomonas* endotoxin.

In some embodiments, the antibody is conjugated to an auristatin or a peptide analog, derivative or prodrug thereof. Auristatins have been shown to interfere with microtubule dynamics, GTP hydrolysis and nuclear and cellular division (Woyke et al (2001) Antimicrob. Agents and Chemother. 45(12): 3580-3584) and have anti-cancer (U.S. Pat. No. 5,663,149) and antifungal activity (Pettit et al., (1998) Antimicrob. Agents and Chemother. 42: 2961-2965. For example, auristatin E can be reacted with para-acetyl benzoic acid or benzoylvaleric acid to produce AEB and AEVB, respectively. Other typical auristatin derivatives include AFP, MMAF (monomethyl auristatin F), and MMAE (monomethyl auristatin E). Suitable auristatins and auristatin analogs, derivatives and prodrugs, as well as suitable linkers for conjugation of auristatins to Abs, are described in, e.g., U.S. Pat. Nos. 5,635,483, 5,780,588 and 6,214,345 and in International patent application publications WO02088172, WO2004010957, WO2005081711, WO2005084390, WO2006132670, WO03026577, WO200700860, WO207011968 and WO205082023.

In some embodiments, the antibody is conjugated to pyrrolo[2,1-c][1,4]-benzodiazepine (PDB) or an analog, derivative or prodrug thereof. Suitable PDBs and PDB derivatives, and related technologies are described in, e.g., Hartley J. A. et al., Cancer Res 2010; 70(17): 6849-6858; Antonow D. et al., Cancer J 2008; 14(3): 154-169; Howard P. W. et al., Bioorg Med Chem Lett 2009; 19: 6463-6466 and Sagnou et al., Bioorg Med Chem Lett 2000; 10(18): 2083-2086.

In some embodiments, the antibody is conjugated to a cytotoxic moiety selected from the group consisting of an anthracycline, maytansine, calicheamicin, duocarmycin, rachelmycin (CC-1065), dolastatin 10, dolastatin 15, irinotecan, monomethyl auristatin E, monomethyl auristatin F, a PDB, or an analog, derivative, or prodrug of any thereof.

In some embodiments, the antibody is conjugated to an anthracycline or an analog, derivative or prodrug thereof. In some embodiments, the antibody is conjugated to maytansine or an analog, derivative or prodrug thereof. In some embodiments, the antibody is conjugated to calicheamicin or an analog, derivative or prodrug thereof. In some embodiments, the antibody is conjugated to duocarmycin or an analog, derivative or prodrug thereof. In some embodiments, the antibody is conjugated to rachelmycin (CC-1065) or an analog, derivative or prodrug thereof. In some embodiments, the antibody is conjugated to dolastatin 10 or an analog, derivative or prodrug thereof. In some embodiments, the antibody is conjugated to dolastatin 15 or an analog, derivative or prodrug thereof. In some embodiments, the antibody is conjugated to monomethyl auristatin E or an analog, derivative or prodrug thereof. In some embodiments, the antibody is conjugated to monomethyl auristatin F or an analog, derivative or prodrug thereof. In some embodiments, the antibody is conjugated to pyrrolo[2,1-c][1,4]-benzodiazepine or an analog, derivative or prodrug thereof. In some embodiments, the antibody is conjugated to irinotecan or an analog, derivative or prodrug thereof.

In some embodiments, the antibody is conjugated to a nucleic acid or nucleic acid-associated molecule. In one such embodiment, the conjugated nucleic acid is a cytotoxic ribonuclease (RNase) or deoxy-ribonuclease (e.g., DNase I), an antisense nucleic acid, an inhibitory RNA molecule (e.g., a siRNA molecule) or an immunostimulatory nucleic acid (e.g., an immunostimulatory CpG motif-containing DNA molecule). In some embodiments, the antibody is conjugated to an aptamer or a ribozyme.

In some embodiments, the antibody is conjugated, e.g., as a fusion protein, to a lytic peptide such as CLIP, Magainin 2, mellitin, Cecropin and P18.

In some embodiments, the antibody is conjugated to a cytokine, such as, e.g., IL-2, IL-4, IL-6, IL-7, IL-10, IL-12, IL-13, IL-15, IL-18, IL-23, IL-24, IL-27, IL-28a, IL-28b, IL-29, KGF, IFNa, IFN3, IFNy, GM-CSF, CD40L, Flt3 ligand, stem cell factor, ancestim, and TNFa.

In some embodiments, the antibody is conjugated to a radioisotope or to a radioisotope-containing chelate. For example, the antibody can be conjugated to a chelator linker, e.g. DOTA, DTPA or tiuxetan, which allows for the antibody to be complexed with a radioisotope. The antibody may also or alternatively comprise or be conjugated to one or more radiolabeled amino acids or other radiolabeled molecules Non-limiting examples of radioisotopes include $^{3}H$, $^{14}C$, $^{15}N$, $^{35}S$, $^{90}Y$, $^{99}Tc$, $^{125}I$, $^{131}I$, $^{186}Re$, $^{213}Bi$, $^{225}Ac$ and $^{227}Th$. For therapeutic purposes, a radioisotope emitting beta- or alpha-particle radiation can be used, e.g., 1311, 90Y, 211At, 212Bi, 67Cu, 186Re, 188Re, and 212Pb.

Techniques for conjugating molecule to antibodies, are well-known in the art (See, e.g., Arnon et al., "Monoclonal Antibodies For Immunotargeting Of Drugs In Cancer Therapy," in Monoclonal Antibodies And Cancer Therapy (Reisfeld et al. eds., Alan R. Liss, Inc., 1985); Hellstrom et al., "Antibodies For Drug Delivery," in Controlled Drug Delivery (Robinson et al. eds., Marcel Deiker, Inc., 2nd ed. 1987); Thorpe, "Antibody Carriers Of Cytotoxic Agents In Cancer Therapy: A Review," in Monoclonal Antibodies '84: Biological And Clinical Applications (Pinchera et al. eds., 1985); "Analysis, Results, and Future Prospective of the Therapeutic Use of Radiolabeled Antibody In Cancer Therapy," in Monoclonal Antibodies For Cancer Detection And Therapy (Baldwin et al. eds., Academic Press, 1985); and Thorpe et al., 1982, Immunol. Rev. 62:119-58. See also, e.g., PCT publication WO 89/12624.) Typically, the nucleic acid molecule is covalently attached to lysines or cysteines on the antibody, through N-hydroxysuccinimide ester or maleimide functionality respectively. Methods of conjugation using engineered cysteines or incorporation of unnatural amino acids have been reported to improve the homogeneity of the conjugate (Axup, J. Y., Bajjuri, K. M., Ritland, M., Hutchins, B. M., Kim, C. H., Kazane, S. A., Halder, R., Forsyth, J. S., Santidrian, A. F., Stafin, K., et al. (2012). Synthesis of site-specific antibody-drug conjugates using unnatural amino acids. Proc. Natl. Acad. Sci. USA 109, 16101-16106; Junutula, J. R., Flagella, K. M., Graham, R. A., Parsons, K. L., Ha, E., Raab, H., Bhakta, S., Nguyen, T., Dugger, D. L., Li, G., et al. (2010). Engineered thio-trastuzumab-DM1 conjugate with an improved therapeutic index to target humanepidermal growth factor receptor 2-positive breast cancer. Clin. Cancer Res. 16, 4769-4778). Junutula et al. (2008) developed cysteine-based site-specific conjugation called "THIOMABs" (TDCs) that are claimed to display an improved therapeutic index as compared to conventional conjugation methods. Conjugation to unnatural amino acids that have been incorporated into the antibody is also being explored for ADCs; however, the generality of this approach is yet to be established (Axup et al., 2012). In particular the one skilled in the art can also envisage Fc-containing polypeptide engineered with an acyl donor glutamine-containing tag (e.g., Gin-containing peptide tags or Q-tags) or an endogenous glutamine that are made reactive by polypeptide engineering (e.g., via amino acid deletion, insertion, substitution, or mutation on the polypeptide). Then a transglutaminase, can covalently cross-link with an amine donor agent (e.g., a small molecule comprising or attached to a reactive amine) to form a stable and homogenous population of an engineered Fc-containing polypeptide conjugate with the amine donor agent being site-specifically conjugated to the Fc-containing polypeptide through the acyl donor glutamine-containing tag or the accessible/exposed/reactive endogenous glutamine (WO 2012059882).

In another aspect, the present invention relates to the humanized antibody of the present invention, as defined in any aspect or embodiment herein, for use as a medicament.

The humanized antibody of the present invention is particularly suitable for the treatment of any disease associated with CLDN1 expression. The humanized antibody of the invention may be used alone or in combination with any suitable agent.

In some embodiments, the humanized antibody of the present invention is particularly suitable for the treatment of viral infections. In some embodiments, the viral infection comprises infection by one or more viruses selected from the group consisting of Arenaviridae, Astroviridae, Birnaviridae, Bromoviridae, Bunyaviridae, Caliciviridae, Closteroviridae, Comoviridae, Cystoviridae, Flaviviridae, Flexiviridae, Hepevirus, Leviviridae, Luteoviridae, Mononegavirales, Mosaic Viruses, Nidovirales, Nodaviridae, Orthomyxoviridae, Picobirnavirus, Picornaviridae, Potyviridae, Reoviridae, Retroviridae, Sequiviridae, Tenuivirus, Togaviridae, Tombusviridae, Totiviridae, Tymoviridae, Hepadnaviridae, Herpesviridae, Paramyxoviridae or Papillomaviridae viruses. In some embodiments, the viral infection comprises infection by one or more viruses selected from the group consisting of adenovirus, rhinovirus, hepatitis, immunodeficiency virus, polio, measles, Ebola, Coxsackie, Rhino, West Nile, small pox, encephalitis, yellow fever, coronavirus, Dengue, influenza (including human, avian, and swine), lassa, lymphocytic choriomeningitis, junin, machuppo, guanarito, hantavirus, Rift Valley Fever, La Crosse, California encephalitis, Crimean-Congo, Marburg, Japanese Encephalitis, Kyasanur Forest, Venezuelan equine encephalitis, Eastern equine encephalitis, Western equine encephalitis, severe acute respiratory syndrome (SARS), parainfluenza, respiratory syncytial, Punta Toro, Tacaribe, pachindae viruses, adenovirus, Dengue fever, influenza A and influenza B (including human, avian, and swine), junin, measles, parainfluenza, Pichinde, punta toro, respiratory syncytial, rhinovirus, Rift Valley Fever, severe acute respiratory syndrome (SARS), Tacaribe, Venezuelan equine encephalitis, West Nile and yellow fever viruses, tick-borne encephalitis virus, Japanese encephalitis virus, St. Louis encephalitis virus, Murray Valley virus, Powassan virus, Rocio virus, louping-ill virus, Banzi virus, Ilheus virus, Kokobera virus, Kunjin virus, Alfuy virus, bovine diarrhea virus, and Kyasanur forest disease. In particular, the humanized anti-Claudin-1 antibody of the present invention may also be used in therapeutic and prophylactic methods to treat and/or prevent HCV infection. The humanized anti-Claudin-1 antibody of the present invention can interfere with HCV-host cells interactions by binding to the extracellular domain of Claudin-1 on a cell surface, thereby reducing, inhibiting, blocking or preventing HCV entry into the cell and/or HCV infection of the cell (WO2010034812). Antibodies of the present invention may be used in a variety of therapeutic or prophylactic methods. In particular, the present invention provides a method for treating or preventing a liver disease or pathology in a subject, which comprises administering to the subject an effective amount of an antibody of the invention which inhibits HCV from entering or infecting the subject's cells, so as to thereby treat or prevent the liver disease or pathology in the subject. The liver disease or pathology may be inflammation of the liver, liver fibrosis, cirrhosis, and/or hepatocellular carcinoma (i.e., liver cancer) associated with HCV infection. The present invention also provides a method for treating or preventing a HCV-associated disease or condition (including a liver disease) in a subject, which comprises administering to the subject an effective amount of an antibody of the invention which inhibits HCV from entering or infecting the subject's cells, so as to thereby treat or prevent the HCV-associated disease or condition in the subject. In certain embodiments of the present invention, the antibody or composition is administered to a subject diagnosed with acute hepatitis C. In other embodiments of the invention, the antibody or composition is administered to a subject diagnosed with chronic hepatitis C. In some embodiments, the methods of the present invention may be used to reduce the likelihood of a subject's susceptible cells of becoming infected with HCV as a result of liver transplant. As already mentioned above, when a diseased liver is removed from a HCV-infected patient, serum viral levels plummet. However, after receiving a healthy liver transplant, virus levels rebound and can surpass pre-transplant levels within a few days. Liver transplant patients may benefit from administration of an inventive antibody that binds to the ectodomain of Claudin-1 on the surface of hepatocytes and thereby reduce, inhibit, block or prevent HCV entry into the cells. Administration may be performed prior to liver transplant, during liver transplant, and/or following liver transplant.

In some embodiments, the humanized antibody of the present invention is suitable for the treatment of hepatocellular carcinomas. In some embodiments, the humanized antibody of the present invention is suitable for the treatment of HCV-associated hepatocellular carcinoma. In some embodiments, the humanized antibody of the present invention is suitable for the treatment of Non-HCV-associated hepatocellular carcinoma.

As used herein the term "hepatocellular carcinoma" or "HCC" refers to the most common type of liver cancer, also called malignant hepatoma. As used herein, the terms "HCV-associated hepatocellular carcinoma" and HCV-associated liver disease" refers to hepatocellular carcinoma and liver disease respectively that are secondary to infection with hepatitis C virus (HCV). The term includes HCC which has developed or initiated following cure of HCV infection. As used herein, the term "non-HCV-associated hepatocellular carcinoma" refers to hepatocellular carcinoma that develops, or that is susceptible of developing, in a patient who has never been infected with HCV. "Non-HCV-associated hepatocellular carcinoma" also includes hepatocellular carcinoma that develops, or that is susceptible of developing, in a patient who has been cured from HCV infection. Similarly, the term "non-HCV-associated liver disease" refers to a liver disease that has developed in a patient who has never been infected with HCV or in patient who has been cured from HCV infection. Examples of non-HCV-associated hepatocellular carcinoma/liver disease include hepatocellular carcinoma/liver disease secondary to hepatitis B virus (HBV) infection, alcoholic liver disease, non-alcoholic fatty liver disease, hereditary hemochromatosis, alpha 1-antitrypsin deficiency, auto-immune hepatitis, some porphyrias, Wilson's disease, aflatoxin exposure, type 2 diabetes, obesity, etc . . . , as well as hepatocellular carcinoma/liver disease of unknown origin. In particular, the present invention provides a method for preventing a patient suffering from a liver disease from developing hepatocellular carcinoma. The liver disease or pathology may be inflammation of the liver, liver fibrosis, and/or cirrhosis. In the practice of the present invention, the underlying cause of the liver disease is not HCV infection. Thus, the invention provides a method for preventing and/or treating non-HCV-associated hepatocellular carcinoma, i.e., for preventing and/or treating hepatocellular carcinoma that develops, or that is susceptible of developing, in a patient who has never been infected with HCV, or in a patient who has been cured from HCV infection. In some embodiments of the invention, the underlying cause of the liver disease is HBV infection. Chronic infection with HBV leads to cirrhosis of the liver and is, with chronic HCV infection, responsible for making liver cancer the most common cancer in many parts of the world. Worldwide, around 2 billion people are infected with HBV. HCC risk is around 20 times higher in people with HBV and/or HCV infection in Western industrialized countries, where prevalence of infection is low. Alternatively, the liver disease may be alcoholic liver disease, where the underlying cause of the liver disease is alcoholism. Alcohol intake has been definitely recognized as a cause of chronic liver diseases, including hepatocellular carcinoma. Alcohol could be involved in the development of HCC through both direct (genotoxic) and indirect mechanisms. An indirect mechanism includes the development of cirrhosis, which is probably the most common pathway to liver carcinogenesis in developed countries. In some embodiments of the preset invention, the underlying cause of the liver disease is non-alcoholic fatty liver disease (NAFLD). NAFLD is the most common liver disorder in the Western industrialized countries. It is considered to be the hepatic manifestation of the metabolic syndrome. Thus, NAFLD tends to develop in people who are overweight or obese, and/or who have diabetes, high cholesterol or high triglycerides. For most people, NAFLD cause no signs and symptoms, and no complications. But in some people with NAFLD, the fat that accumulates in the liver can cause inflammation and scarring in the liver that is believed to result in fibrosis and cirrhosis. This more serious form of NAFLD is sometimes called non-alcoholic steatohepatitis (NASH). It is worth noting that metabolic syndrome and type 2 diabetes have been demonstrated to be independent risk factors of HCC. In some embodiments, the underlying cause of the liver disease is an inherited metabolic disease, such as hereditary hemochromatosis. People with hereditary hemochromatosis absorb too much iron from their food. The iron settles in tissues throughout the body, including the liver. If enough iron builds up in the liver, it can lead to cirrhosis. Other inherited metabolic diseases that are risk factors for hepatocellular carcinoma include, alpha 1 antitrypsin deficiency, porphyria cutanea tarda, Wilson's disease, tyrosinemia, and glycogen storage diseases. In some embodiments, the underlying cause of the liver disease is autoimmune hepatitis (also called lupoid hepatitis). Autoimmune hepatitis is a chronic disease of the liver that occurs when the body's immune system attacks cells of the liver causing the liver to be inflamed. Another autoimmune disease that affects the liver and can cause cirrhosis is primary biliary cirrhosis or PBC. PBC is an autoimmune condition, in which the immune system slowly attacks the bile ducts in the liver. When the bile ducts are damaged, bile builds up in the liver and over time damages the tissue. This can lead to scaring, fibrosis and cirrhosis. In some embodiments, the underlying cause of liver disease is exposure to aflatoxins. Aflatoxins are poisons produced by a fungus that grows on crops (such as peanuts, wheat, soybeans, corn, and rice) that are stored poorly. Long term exposure to these substances is a major risk for liver cancer. The risk is increased even more in people with HCV or HBV infection. In developed countries, the content of aflatoxin in foods is regulated through testing. Aflatoxin contamination is more common in certain parts of Africa and Asia. In some embodiments, the underlying cause of liver disease is unknown or the liver disease is caused by yet to be discovered agents including agents of genetic origin, infectious agents or chemical and/or physical liver toxic agents.

In some embodiments, the humanized anti-CLDN1 antibody of the present invention may be used for the treatment of cancer, in particular colorectal cancer. Cancer diseases associated with CLDN1 overexpression typically include but are not limited to colorectal cancer, gynaecological cancers, ovarian cancers, cervical neoplasias, melanoma, squamous cell carcinoma (SCC) as oral SCC, lower lip SCC, head and neck, skin SCC, Tonsillar SCC, gastric adenocarcinoma, thyroid carcinoma, mammary carcinoma, Neuroepithelial papillary tumor of the pineal region (PTPR), clear cell renal cell carcinoma, mucoepidermoid carcinoma (MEC) of salivary gland, nasopharyngeal carcinoma, urothelial carcinoma of the upper urinary tract, esophageal carcinoma, mesotheliomas, pleural metastatic adenocarcinoma, and some pancreas tumors.

In some embodiments, the humanized antibody of the present invention is suitable for the treatment of liver disease.

In some embodiments, the humanized antibody of the present invention is suitable for the treatment of fatty liver disease (FLD).

In some embodiments, the humanized antibody of the present invention is suitable for the treatment of nonalcoholic fatty liver disease" (NAFLD).

In some embodiments, the humanized antibody of the present invention is suitable for the treatment of non-alcoholic steatohepatitis (NASH).

The term "liver disease" has its general meaning in the art and refers to liver inflammation, liver scarring, liver steatosis, liver fibrosis, fatty liver disease" (FLD), nonalcoholic fatty liver disease" (NAFLD), non-alcoholic steatohepatitis (NASH) or cirrhosis.

As used herein, the term "fatty liver disease" (FLD) or "hepatic steatosis" has its general meaning in the art and refers to "alcoholic fatty liver disease", "nonalcoholic fatty liver disease" (NAFLD) and nonalcoholic steatohepatitis (NASH). NAFLD is an evolutive condition which may encompass different forms of lesions, ranging from simple steatosis (also referred herein as "nonalcoholic fatty liver", or NAFL) to nonalcoholic steatohepatitis (NASH), liver fibrosis, cirrhosis, and hepatocellular carcinoma (HCC).

As used herein, the term "NASH" has its general meaning in the art and refers to non-alcoholic steatohepatitis. Chronic inflammation and fibrosis are key features of NASH. NASH has potential for fibrosis, cirrhosis decompensation, and hepatocellular carcinoma.

As used herein, the term "treatment" or "treat" refer to both prophylactic or preventive treatment as well as curative or disease modifying treatment, including treatment of subject at risk of contracting the disease or suspected to have contracted the disease as well as subjects who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a subject during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a subject during treatment of an illness, e.g., to keep the subject in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., disease manifestation, etc.]).

By a "therapeutically effective amount" of the antibody of the invention is meant a sufficient amount of the antibody to treat said cancer, at a reasonable benefit/risk ratio applicable to any medical treatment. It will be understood, however, that the total daily usage of the antibodies and compositions of the present invention will be decided by the attending physician within the scope of sound medical judgment. The specific therapeutically effective dose level for any particular patient will depend upon a variety of factors including the disorder being treated and the severity of the disorder; activity of the specific antibody employed; the specific composition employed, the age, body weight, general health, sex and diet of the patient; the time of administration, route of administration, and rate of excretion of the specific antibody employed; the duration of the treatment; drugs used in combination or coincidental with the specific antibody employed; and like factors well known in the medical arts. For example, it is well known within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Typically, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

For administration, the humanized antibody of the present invention is formulated as a pharmaceutical composition. A pharmaceutical composition comprising a humanized antibody of the present invention can be formulated according to known methods to prepare pharmaceutically useful compositions, whereby the therapeutic molecule is combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. (See, e.g., Gennaro (ed.), Remington's Pharmaceutical Sciences (Mack Publishing Company, 19th ed. 1995)) Formulations may further include one or more excipients, preservatives, solubilizers, buffering agents, albumin to prevent protein loss on vial surfaces, etc. The form of the pharmaceutical compositions, the route of administration, the dosage and the regimen naturally depend upon the condition to be treated, the severity of the illness, the age, weight, and sex of the patient, etc. The pharmaceutical compositions of the present invention can be formulated for a topical, oral, parenteral, intranasal, intravenous, intramuscular, subcutaneous or intraocular administration and the like. Typically, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. The doses used for the administration can be adapted as a function of various parameters, and in particular as a function of the mode of administration used, of the relevant pathology, or alternatively of the desired duration of treatment. To prepare pharmaceutical compositions, an effective amount of the humanized antibody of the present invention may be dissolved or dispersed in a pharmaceutically acceptable carrier or aqueous medium. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin. Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The preparation of more, or highly concentrated solutions for direct injection is also contemplated, where the use of DMSO as solvent is envisioned to result in extremely rapid penetration, delivering high concentrations of the active agents to a small tumor area. Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. The humanized antibodies of the present invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered. In addition to the compounds formulated for parenteral administration, such as intravenous or intramuscular injection, other pharmaceutically acceptable forms include, e.g. tablets or other solids for oral administration; time release capsules; and any other form currently used. In some embodiments, the use of liposomes and/or nanoparticles is contemplated for the introduction of antibodies into host cells. The formation and use of liposomes and/or nanoparticles are known to those of skill in the art. Nanocapsules can generally entrap compounds in a stable and reproducible way. To avoid side effects due to intracellular polymeric overloading, such ultrafine particles (sized around 0.1 µm) are generally designed using polymers able to be degraded in vivo. Biodegradable polyalkyl-cyanoacrylate nanoparticles that meet these requirements are contemplated for use in the present invention, and such particles may be are easily made. Liposomes are formed from phospholipids that are dispersed in an aqueous medium and spontaneously form multilamellar concentric bilayer vesicles (also termed multilamellar vesicles (MLVs)). MLVs generally have diameters of from 25 nm to 4 µm. Sonication of MLVs results in the formation of small unilamellar vesicles (SUVs) with diameters in the range of 200 to 500 Å, containing an aqueous solution in the core. The physical characteristics of liposomes depend on pH, ionic strength and the presence of divalent cations.

The invention will be further illustrated by the following figures and examples. However, these examples and figures should not be interpreted in any way as limiting the scope of the present invention.

FIGURES

FIG. 1. Sequence analysis of the variable region of the heavy and the light chains of rat anti-CLDN1 mAb OM-7D3-B3. (A) Alignment of protein sequences of rat OM-7D3-B3 heavy chain (top) (SEQ ID NO:3) and light chain (bottom) (SEQ ID NO:4) with the nearest rat germline sequence (SEQ ID NO:5 and SEQ ID NO:6). The most closely matched germline sequences had homology of 86.7% and 90.5% with heavy and light chain, respectively. (B) Sequence alignment of rat OM-7D3-B3 heavy (top) (SEQ ID NO:3) and light (bottom) (SEQ ID NO:4) chain with the nearest human germline sequences (SEQ ID NO:7 and SEQ ID NO:8). Also shown are the humanized variants of heavy (H1, H2 and H3) (SEQ ID NO: 9; SEQ ID NO: 11 and SEQ ID NO: 1) and light (L1, L2 and L3) (SEQ ID NO: 10; SEQ ID NO: 12 and SEQ ID NO: 2) chains that were generated in the process of humanizing rat OM-7D3-B3. The closest germline sequences were identified using IGBLAST tool (www.ncbi.nlm.nih.gov/igblast/igblast.cgi). The complementarity-determining regions (CDRs) are highlighted in yellow and the joining (J)-region that connects the CDR3 and the constant domain of heavy and light chains is shown in pink. The framework region (FR), CDRs and the J-region are indicated.

FIG. 2. Humanized anti-CLDN1 mAbs specifically bind to CLDN1 and potently inhibit HCV infection. (A) Flow cytometry analysis of the binding of humanized OM-7D3-B3 anti-CLDN1 mAbs (20 µg/mL) to cell lines. Humanized antibodies specifically bind to Huh7.5.1 and HepG2 cells expressing human CLDN1 but not to 293T cells lacking CLDN1 expression. Binding is expressed as delta median fluorescence intensity (ΔMFI). (B) H3L3 specifically binds to exogenous CLDN1 expressed on 293T cells. CLDN-null 293T cells were transfected with either empty or CLDN1-expressing pcDNA3.1 vector. After 48 h, cells were stained with isotype control, rat OM-7D3-B3 or humanized H3L3 antibody (20 µg/mL). The ΔMFI from one experiment performed in duplicate are shown. (C) All nine humanized anti-CLDN1 mAbs potently inhibit HCVcc infection. Huh 7.5.1 cells were incubated with different mAbs (25 µg/mL) at 37° C. for 1 h prior to infection with HCVcc. Infectivity was assessed after 72 h by measuring luciferase activity and is expressed as log relative luciferase units (RLU). (D) Humanized anti-CLDN1 mAbs inhibit entry of HCVpp bearing envelope glycoproteins of strains H77 (genotype 1a) and HCV-J (genotype 1b). PHH were pre-treated with the humanized antibodies (20 µg/mL) for 1 h at 37° C. prior to infection with HCVpp. Infectivity was measured by luciferase activity after 72 h and is expressed as RLU. Graphs show results from one experiment performed in duplicate (A, B, D) or in triplicate (C).

FIG. 3. Functional characterization of the humanized anti-CLDN1 antibody clone H3L3 in cell culture. (A) H3L3 potently and dose-dependently inhibits HCV infection. Huh7.5.1 cells incubated with increasing concentrations of rat OM-7D3-B3, humanized H3L3 or isotype control antibodies prior to infection with HCVcc (Jc1 wild type, Jc1-A156S or Jc1-R155K). Infection was assessed by measuring luciferase activity after 72 h. Results are expressed as log RLU from three independent experiments performed in triplicate. (B, C) H3L3 inhibits HCV cell-cell transmission, like the parent rat antibody. Huh7.5.1 cells were electroporated with HCV Jc1 RNA (producer cells) and co-cultured with naïve Huh7.5.1-GFP cells (target cells) in the presence of control or anti-CLDN1 antibody (11 µg/mL). The co-cultured cells were fixed with PFA after 24 h and stained with an NS5A antibody (B). The extent of cell-cell transmission was determined by calculating percentage of GFP+ NS5A+ cells (C). Results from a single experiment performed in duplicate are shown. (D) H3L3 synergizes with DAA. Huh7.5.1 cells were pre-treated with H3L3 in combination with sofosbuvir (SOF) or daclatasvir (DCV) prior to infection with HCVcc. Infection was assessed after 72 h by luciferase activity. Synergy (defined as an inhibition of 20% above that expected for additive effects, shown in black) was assessed according to the Prichard and Shipman method. Results from a representative experiment are shown.

Figure 4:
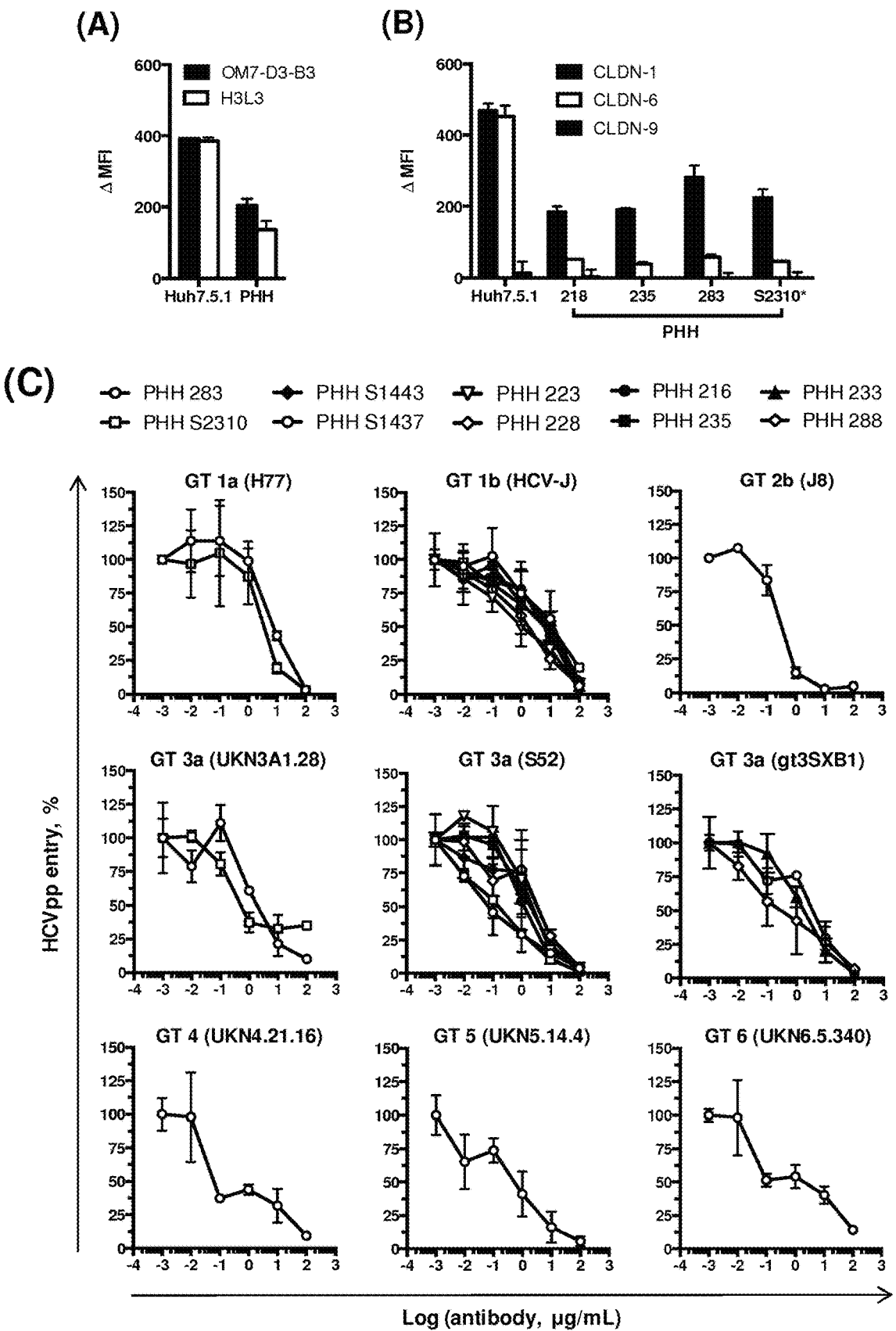

FIG. 4. H3L3 pan-genotypically inhibits HCVpp infection of PHH without escape. (A) H3L3, like the parent antibody, binds to PHH as well as Huh7.5.1 cells. Cells were stained with isotype control, rat OM-7D3-B3 or humanized H3L3 antibody (20 µg/mL). The ΔMFI from one experiment performed in duplicate are shown. (B) PHH express only very low surface levels of CLDN6 and CLDN9. PHH from donors subsequently tested in inhibition experiments were treated with isotype control or CLDN1-, CLDN6- or CLDN9-specific mAbs (20 µg/mL). Expression of CLDN1, CLDN6 and CLDN9 is shown as ΔMFI. (C) H3L3 inhibits HCVpp infection of PHH, without escape. PHH from up to ten different donors were treated with H3L3 for 1 h prior to infection with HCVpp. Infection was assessed by luciferase activity after 72 h. Results show one experiment performed in duplicate (PHH) or two independent experiments performed in triplicate (Huh7.5.1).

FIG. 5. H3L3 cures chronically HCV infected human-liver chimeric uPA-SCID mice. (A) Two mice chronically infected with HCV Jc1 were treated with 500 µg of H3L3 anti-CLDN1 mAb weekly for four weeks. As a control, one mouse was similarly treated with isotype control human antibody. Human albumin (B) and IgG4 (C) levels were monitored. Red+symbols indicate the times of antibody treatment.

EXAMPLES

Example 1

Material & Methods

Sequencing of the Variable Region of Rat Anti-CLDN1 mAb OM-7D3-B3.

Total RNA was isolated in pure RNase-free water from $10^7$ hybridoma cells using the Qiagen RNeasy mini kit. $V_H$ and $V_L$ cDNAs were prepared using primers derived from the constant domain (CH1) of rat IgG2b and rat kappa light chain by reverse transcription. cDNAs were amplified using a pool of primers corresponding to the signal sequence region and subsequently cloned into pGem-T Easy vector (Promega). Clones were screened for inserts and the DNA sequence determined by sequencing. CDRs were identified with reference to other antibody sequences as described (29).

Humanization of Rat Anti-CLDN1 mAb OM-7D3-B3 and Antibody Production.

Humanization was performed by CDR grafting as described (30, 31). Briefly, the human germline $V_H$ and $V_K$ sequences most similar to the rat anti-CLDN1 mAb OM-7D3-B3 in the IMGT database were identified using the IGBLAST tool (www.ncbi.nlm.nih.gov/igblast/) (FIG. 1A). The CDRs of mAb OM-7D3-B3 were engrafted on framework regions of the identified $V_H$ and $V_K$ human germline sequence. Additionally, framework regions of anti-CLDN1 mAb OM-7D3-B3 were compared with rat germline sequences to identify major sequence variations that could potentially contribute to antibody specificity. These amino acids in the framework regions were preserved or changed (either alone or in groups) to the ones present in the most similar human germline sequence. In this manner, three variants each of heavy chain (H1, H2, H3) and light chain (L1, L2, L3) were generated in the first round of humanization (FIG. 1B). These $V_H$ and $V_K$ variants were fused in-frame with constant domains of the human IgG4 heavy and human kappa light chains, respectively, and cloned into an appropriate mammalian expression vector. Nine full-length humanized antibodies (H1L1, H1L2, H1L3, H2L1, H2L2, H2L3, H3L1, H3L2 and H3L3) were produced by co-transfecting plasmids containing the appropriate heavy and light chain variants into Chinese hamster ovary (CHO) cells. Supernatants were harvested and antibodies purified using the MAbTrap Kit (GE healthcare). The antibodies were buffer-changed into PBS prior to their use in subsequent experiments.

Cells and Viruses.

Huh7.5.1 (16), HepG2 (32) and human embryonic kidney 293T (33) cells were cultured as described. Production of HCVpp (34) bearing envelope glycoproteins of strains H77, HCV-J, JFH1, J8, NIH S52, UKN3A1.28, UKN4.21.16, UKN5.14.4, UKN6.5.340 has been described previously. Strain gt3SXB1 (genotype 3) was cloned from the serum of a patient chronically infected with HCV and consulting at the Strasbourg University Hospitals. E1E2 sequences were amplified and inserted into the phCMV IRES vector using EcoRV restriction sites as described for HCV-AD78 (33). Production of luciferase reporter HCVcc (Luc-Jc1) as well as DAA-resistant mutants Luc-Jc1-A156S, Luc-Jc1-R155K and Luc-Jc1-Y93H has been described (23, 35).

Primary Human Hepatocytes (PHH).

PHH were isolated from liver tissue obtained from patients undergoing liver resection at the Strasbourg University Hospitals. Informed consent was obtained and protocols were approved by the local ethics committee at Strasbourg University Hospitals (CPP 10-17). PHH were isolated and cultured as described (24).

Flow Cytometry.

To evaluate binding of the humanized antibodies to CLDN1 expressed on Huh7.5.1, HepG2 and 293T cells, $2 \times 10^5$ cells were incubated with 20 µg/mL anti-CD81 mAb JS-81 (BD Biosciences), rat anti-CLDN1 mAb OM-7D3-B3, humanized anti-CLDN1 mAb or PBS for 1 hour at room temperature. Cells were washed and incubated with phycoerythrin (PE)-conjugated species-specific secondary antibodies at 4° C. for 45 min to allow detection of binding. Cells were subsequently washed and fixed with 2% paraformaldehyde (PFA) prior to analysis by flow cytometry using a BD LSRII flow cytometer. Net delta median fluorescence intensities (ΔMFI) were obtained after subtracting the background fluorescence with PBS. To evaluate the specificity of binding, 293T cells were transfected either with empty vector or with pcDNA3.1 encoding human CLDN1. After 48 h, binding of antibodies was assessed as described above.

We also evaluated binding of the humanized antibody clone H3L3 to PHH, as well as expression of CLDN subtypes on the surface of PHH. Cryopreserved PHH (from the same donors as used in inhibition experiments) were treated with CLDN-specific mAbs (CLDN1, rat OM-7D3-B3 or humanized H3L3; CLDN6, rat WU-9E1-G2; CLDN9, rat YD-4E9-A2) or control isotype antibody at 20 µg/mL, as described (28). Cells were then stained with a species-specific PE-conjugated secondary antibody to detect binding. After washing, cells were fixed with 2% PFA and analysed by flow cytometry (FACscan). In all experiments, Huh7.5.1 cells and PHH were analyzed in parallel.

Inhibition Assays with Humanized Anti-CLDN1 mAb.

Huh7.5.1 or PHH were pre-incubated with antibodies (control mAb, rat OM-7D3-B3 and humanized H3L3; serial dilutions from 100 µg/mL to 0.001 µg/mL were tested) for 1 h at 37° C. and subsequently exposed to HCVcc or HCVpp, respectively. For HCVpp experiments, PHH from several different donors were evaluated. Following the treatment, cells were infected with HCVpp for 4 h at 37° C. Infection was analyzed by measuring intracellular luciferase activity after 72 h, expressed as relative light units (RLU).

Cell-Cell Transmission Assay.

The HCV cell-cell transmission assay has been described (36). Briefly, Huh7.5.1 cells were electroporated with HCV Jc1 RNA (virus-producer cells) and co-cultured with uninfected Huh7.5 target cells stably expressing green fluorescent protein (GFP) in the presence of humanized anti-CLDN1 clone H3L3 anti-CLDN1, rat anti-CLDN1 clone OM-7D3-B3 or isotype control mAb (11 µg/mL). Cell-free transmission was blocked by a neutralizing HCV anti-E2 mAb, AP33 (25 µg/mL). Twenty-four hours later, cells were fixed with 2% PFA and stained with an NS5A-specific antibody (Virostat, 0.1 µg/mL). De novo infection (GFP and NS5A double positive cells) was assessed by flow cytometry (BD LSRII). Cell-cell transmission was presented as a percentage of GFP+NS5A+ infected cells relative to Huh7.5-GFP+ target cells in the presence of HCV anti-E2 mAb AP33.

Assessment of Antiviral Synergy.

The humanized anti-CLDN1 antibody H3L3 was tested in combination with DAAs in the HCVcc (Jc1-Luc) model as described previously (22). Huh7.5.1 cells were pre-treated with H3L3 in combination with sofosbuvir or daclatasvir for 1 h at 37° C. prior to incubation with HCVcc in the presence of combined compounds for 4 h at 37° C. Viral infection was assessed 72 h later by luciferase activity. Synergy was assessed using the Prichard and Shipman method (37). Inhibition greater than 20% above the level expected from additive effects indicates significant synergy (37).

HCV Infection and Treatment of Human-Liver Chimeric uPA-SCID Mice.

Experiments were performed according to local ethics committee approval (CREMEAS, project numbers 02014120416254981 (APAFIS #72.02) and 02014120511054408 (APAFIS #74.03)) at the Inserm U1110 animal facility. Severe combined immunodeficient mice homologous for urokinase-type plasminogen activator expression under the control of mouse albumin promoter (uPA-SCID) were engrafted with PHH as described (38). Human liver-chimeric uPA-SCID mice were then infected with HCVcc (Jc1; genotype 2a) by intraperitoneal (ip) injection as described (21). Three weeks after infection, mice were given ip injections of 25 mg/kg humanized H3L3 or isotype control mAb at weekly intervals for 4 weeks (21). Plasma HCV RNA, human albumin and IgG4 levels were monitored as described (21).

Results:

Humanization of Anti-CLDN1 Antibody OM-7D3-B3.

The rat anti-CLDN1 mAb OM-7D3-B3 described previously efficiently inhibits HCV infection in vitro and in vivo (20, 21). Moreover, this antibody demonstrated no toxicity or adverse effects in human liver-chimeric uPA-SCID and immunocompetent Balb/c mice (21). To further the clinical development of this mAb, we humanized it into the human IgG4 subtype. To this end, cDNA recovered from hybridoma cells was sequenced to identify the VH and VL genes. The VH and VL of rat OM-7D3-B3 were derived from $V_H5$ (IGHV5S49*01) and $V_K6$ (IGKV6S11*01) gene families that underwent rearrangement with the $J_H2$ (IGHJ2*01) and $J_K1$ (IGKJ1*01) families of J-segment genes respectively (FIG. 1A). To ascertain the functionality of VH and VL sequences, we produced a recombinant full-length IgG2b (parent isotype) antibody in CHO cells and characterized its binding and inhibitory properties. Indeed, this antibody was able to bind to CLDN1 and to inhibit HCVcc infection (data not shown), confirming the functionality of the sequences and thereby allowing us to proceed with humanization.

We humanized the VH and VL chains by modifying the residues in the framework region while keeping the CDRs intact. To facilitate this, we first identified the most similar human germline VH and VL amino acid sequences by comparison with the sequences in the IMGT database using IGBLAST tool (www.ncbi.nlm.nih.gov/igblast/). The most closely matching human Ig germline V sequences were IGHV3-21*01 for VH and IGKV3-15*01 for VL, with corresponding homology of 83.7% and 64.5%, respectively (FIG. 1A). Using these human germline sequences as a guide, we generated different variants of heavy and light chains by CDR engraftment. These variants were cloned into a vector bearing the constant domains of human IgG4 to produce a panel of nine full-length antibodies with different heavy and light chain combinations (FIG. 1B), which we referred to as H1L1, H1L2, H1L3, H2L1, H2L2, H2L3, H3L1, H3L2 and H3L3. Recombinant full-length antibodies were produced by transient co-transfection of CHO cells with plasmids containing the humanized heavy and light chain variable domains of rat anti-CLDN1 antibody OM-7D3-B3 and human IgG4 constant domains. The antibodies were purified from the supernatant using protein G columns provided in the MAbTrap Kit (GE healthcare), followed by buffer exchange to PBS. We then tested the ability of these antibodies to bind to CLDN1 expressed on the surface of Huh7.5.1 and HepG2 cells; 293T cells that do not express CLDN1 were used as a negative control. As shown in FIG. 2A, the humanized antibodies bound to Huh7.5.1 and HepG2 cells but not to CLDN1-negative 293T cells. The binding profile of the humanized antibodies was similar to the parent rat anti-CLDN1 antibody. The clone H3L3 was selected to investigate the binding specificity of the humanized antibodies. We transfected 293T cells with plasmid encoding human CLDN1 and compared antibody binding to the parental CLDN1-deficient 293T cells. As observed for the parental rat antibody, the humanized anti-CLDN1 mAb H3L3 bound to 293T cells overexpressing human CLDN1 but not to the control cells transfected with an empty vector (FIG. 2B).

Antiviral Activity of Humanized CLDN1-Specific Antibodies.

We next assessed the anti-HCV activity of panel of humanized antibodies in HCVcc inhibition assays. As expected based on their binding profile, all nine humanized antibodies potently inhibited HCVcc infection of Huh7.5.1 cells at 25 µg/mL (FIG. 2C). To investigate if the humanized antibodies inhibited HCV entry in a more physiological context, we tested the ability of these antibodies to inhibit HCVpp infection of PHH, using pseudoparticles bearing genotype 1a and 1b envelope glycoproteins. All antibodies inhibited HCVpp entry into PHH at 20 µg/mL (FIG. 2D). Furthermore, the anti-HCV activities of all humanized antibodies were most similar to those of the parental rat antibody. Taken together, these data indicate that all nine humanized antibodies are functionally similar to the original rat anti-CLDN1 mAb OM-7D3-B3.

We generated a second panel of nine antibodies derived from different combinations of three additional humanized light and heavy chain variants. All nine additional antibodies were found to be equally potent at inhibiting HCVcc infection of Huh7.5.1 cells in a dose-dependent manner (data not shown). As none of the changes made in the framework regions of these 18 humanized antibodies had any impact on their anti-HCV activities, we conclude that the functional residues of rat mAb OM-7D3-B3 are likely located in the CDRs.

H3L3 Efficiently Inhibits HCV Infection and Spread.

We selected the humanized anti-CLDN1 mAb clone H3L3 for detailed functional characterization, based on its favourable binding and inhibitory properties. We first compared the dose-response profiles of the humanized anti-CLDN1 mAb H3L3 and the parental rat OM-7D3-B3 antibody, using HCVcc (Luc-Jc1; genotype 2a) and Huh7.5.1 cells. The humanized anti-CLDN1 H3L3 potently and dose-dependently inhibited HCVcc infection of Huh7.5.1 cells, with a remarkably similar profile to the parental rat anti-CLDN antibody (FIG. 3A). Furthermore, both H3L3 and OM-7D3-B3 inhibited infection by DAA-resistant HCVcc NS3 mutants Jc1-A156S and Jc1-R155K (FIG. 3A). Both antibodies were equally potent against DAA-resistant HCVcc and wild-type HCVcc (FIG. 3A).

Considering the important role of cell-cell transmission in HCV persistence and the previously demonstrated ability of the rat anti-CLDN1 mAb OM-7D3-B3 to block this route of HCV entry (21), we tested humanized anti-CLDN1 mAb H3L3 in a cell-cell transmission assay. As expected, H3L3 efficiently blocked cell-cell transmission of HCV (FIG. 3B), with similar potency as observed for the rat mAb OM-7D3-B3 (FIG. 3C). These data indicate that the humanized anti-CLDN1 mAb H3L3 has the same efficacy as the parent rat antibody.

Figure 3D:
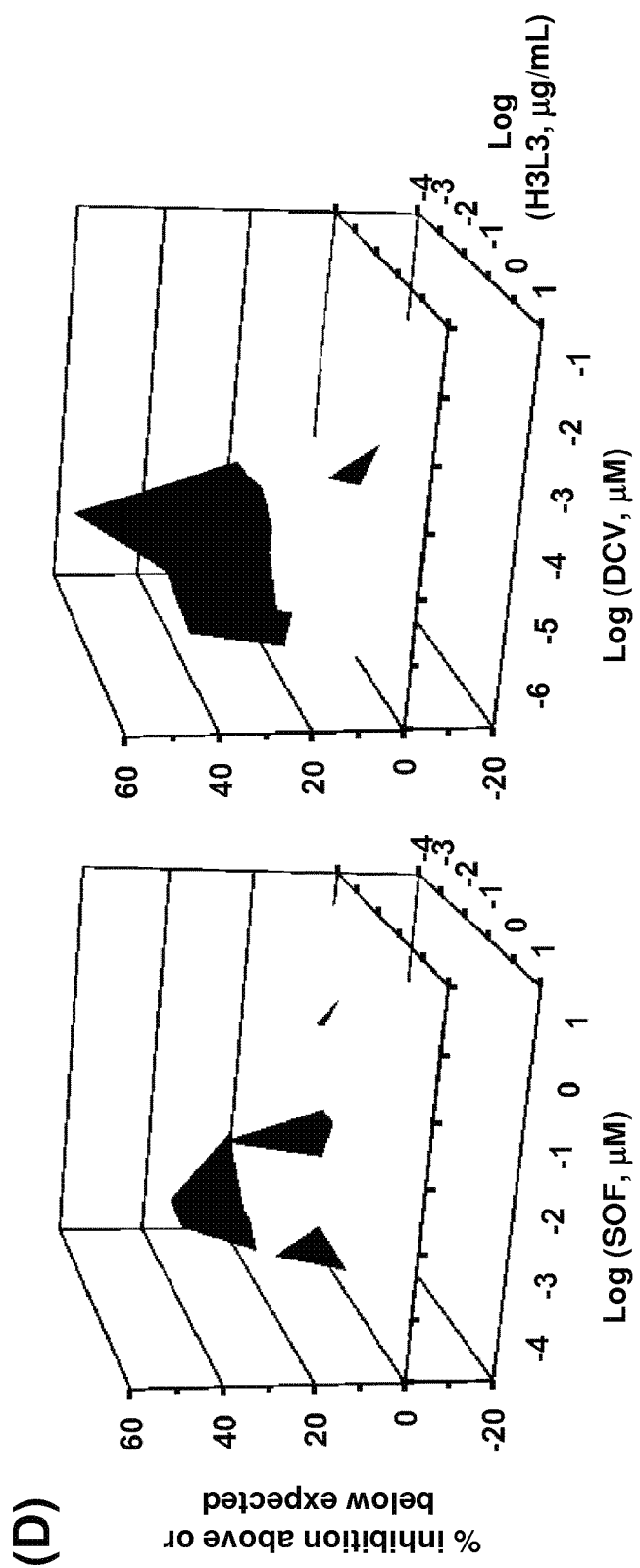

Previous work demonstrated antiviral synergy between the rat anti-CLDN1 mAb OM-7D3-B3 and DAAs (22), an attractive feature in combination therapies. We used the Prichard method (37) to determine if the humanized anti-CLDN1 mAb H3L3 retains the ability to synergize with DAA. Indeed, combining H3L3 with sofosbuvir or daclatasvir resulted in significant synergistic activity (FIG. 3D).

H3L3 Pan-Genotypically Inhibits HCVpp Infection of PHH, without Detectable Escape.

Given that escape from CLDN1-directed therapies has been reported previously for some genotypes of HCV in CLDN6- and/or CLDN9-expressing cell lines (25-27), we investigated the physiological relevance of escape in the context of PHH, using the H3L3 antibody. We first used flow cytometry analysis to confirm that H3L3 binds to PHH (FIG. 4A), as observed previously for the parental rat antibody. We next evaluated expression levels of CLDN6 and CLDN9 on PHH from four different donors, based on previous observations that PHH express negligible levels of CLDN6 and CLDN9 (28). Indeed, flow cytometry analysis revealed that the PHH from these four donors (PHH 218, 235, 283 and S2310) expressed only very low surface levels of CLDN6, in contrast to robust CLDN6 expression in Huh7.5.1 cells (FIG. 4B). Neither PHH nor Huh7.5.1 cells expressed detectable CLDN9 (FIG. 4B).

We then evaluated the functional relevance of this low CLDN6 expression in PHH. Using the HCVpp system, we tested entry of all major genotypes into PHH (donor 283). H3L3 pan-genotypically inhibited HCVpp infection of PHH, without detectable escape (FIG. 4C). To further exclude the possibility of escape, we isolated PHH from nine additional donors, including PHH 235 and S2310, which had very low or negligible levels of surface CLDN6 and CLDN9 surface expression (FIG. 4B). We selected one strain of genotype 1b and three strains of genotype 3a for further evaluation, as these genotypes are prone to escape from CLDN1 (27). Furthermore, genotype 3a is currently difficult to treat and associated with rapid progression to severe liver disease (2). We did not detect any escape for either genotype in any of the PHH tested (FIG. 4C). Thus, escape from CLDN1 antibodies in vivo is likely precluded by low surface expression levels of CLDN6 and likely not to be relevant in the context of the human liver.

H3L3 Cures Chronic HCV Infection in Human-Liver Chimeric uPA-SCID Mice.

Finally, we evaluated the in vivo efficacy of the humanized anti-CLDN1 mAb H3L3 by testing its ability to cure human liver-chimeric uPA-SCID mice chronically infected with HCV. Chronically HCV-infected mice were given weekly ip injections of 25 mg/kg of humanized anti-CLDN1 mAb H3L3 (n=2) or isotype control human IgG4 mAb (n=1) for 4 weeks. All CLDN1-specific mAb H3L3-treated mice showed undetectable HCV RNA levels at the end of the study period (FIG. 5A). Stable human albumin levels in treated mice confirmed engraftment of human PHH (FIG. 5B) and indicated that the H3L3 antibody did not affect liver function (FIG. 5C). Therefore, the humanized CLDN1-specific mAb H3L3 induces clearance of chronic HCV infection, as observed for the parental rat anti-CLDN1 mAb OM-7D3-B3 (21). Collectively, our data demonstrate the successful humanization of the rat anti-CLDN1 mAb, thereby paving the way for its clinical development.

Discussion:

We previously reported the production of rat anti-CLDN1 mAbs with potent and broad anti-HCV activity in vitro and in vivo (20, 21, 24). To facilitate the clinical development of these antibodies for anti-HCV therapy, we humanized our lead rat anti-CLDN1 mAb OM-7D3-B3. We generated humanized antibodies by grafting CDRs of rat anti-CLDN1 mAb OM-7D3-B3 on the backbone of human IgG4. We evaluated the residues in the framework regions with potential roles in antibody function. While we noted that both the light and the heavy chain of the rat anti-CLDN1 mAb had major germline variations in the sequence at several places, amino acids changes at these locations appeared to be well-tolerated. The heavy chain was relatively easy to humanize with fewer substitutions needed (e.g. 9 substitutions between rat and the humanized H3 variant) compared to the light chain (e.g. 18 substitutions between rat and the humanized L3 variant). Moreover, we found that antibodies consisting of humanized heavy or light chains paired with chimeric (rat variable domains and human IgG4 constant domains) light or heavy chains, respectively, not only bound to CLDN1 but were also equally potent at inhibiting HCVcc infection of Huh7.5.1 cells. This strongly suggests that anti-CLDN1 mAb OM-7D3-B3 is highly tolerant to substitutions in the framework region in terms of pairing between the heavy and the light chains, as is reflected by its activity. Interestingly, during the preparation of this manuscript, a phage display screen identified human single chain antibody fragments that bound to CLDN1 (39). Twelve clones were converted to human IgG4, some of which inhibited HCVcc infection of Huh7.5 cells (39). However, the activity of these antibodies in PHH and in animal models remains to be determined.

Notably, all of the humanized antibodies that we generated were able to bind CLDN1 and inhibit HCVcc infection with similar potency. We selected the mAb H3L3 for detailed characterization and found it to be as potent as the parent rat antibody, in terms of inhibiting HCVcc infection and HCVpp entry of different genotypes, blocking cell-cell transmission, and curing chronically HCV-infected human liver-chimeric uPA-SCID mice. Given that genotype-dependent escape from CLDN1-targeted therapies through CLDN6 and/or CLDN9 has been described in cell lines (25-27), we evaluated the functional relevance of escape using the H3L3 antibody in PHH. H3L3 potently and pan-genotypically inhibited HCVpp infection of PHH from up to ten different donors, without any detectable escape (FIG. 4C). The lack of escape in PHH reflects low surface expression levels of CLDN6 and CLDN9 (FIG. 4B), consistent with highly variable CLDN6 mRNA expression in the liver of infected patients (27), lack of CLDN6 protein expression in liver sections (28) and lack of CLDN6 and CLDN9 protein expression in primary hepatocytes (26).

Thus, escape from CLDN1-directed therapies such as the H3L3 antibody is likely not relevant in vivo, at least for the majority of patients.

Any newly developed antiviral for HCV would likely be incorporated into a combination therapy regimen. Importantly, H3L3 synergized with currently approved DAAs, sofosbuvir and daclatasvir (FIG. 3D), and H3L3 was also active against DAA-resistant HCV NS3 mutants (FIG. 3A). These are attractive features for a potential combination therapy. We also show that H3L3 is active against different isolates of genotype 3a, which is currently difficult-to-treat and associated with more severe liver disease (2). H3L3 thus represents a novel treatment strategy for patients with treatment failure.

Humanization of anti-CLDN1 mAb OM-7D3-B3 is the first step towards its clinical development. Any potential anti-receptor antibody will have to be safe, without any antibody-mediated effector functions, and non-immunogenic. In order to avoid destruction of healthy hepatocytes from antibody-mediated effector functions, we humanized anti-CLDN1 mAb OM-7D3-B3 into the IgG4 isotype, which can neither sensitize natural killer (NK) cells nor activate the complement system. Thus, IgG4 does not induce antibody-dependent cell-mediated cytotoxicity or complement-mediated lysis of target cells. Although humanization of the rat antibody in itself is likely to reduce its immunogenicity in humans, the antibody will require further evaluation in an appropriate animal model with an immune system closer to humans, such as non-human primates. Targeting any host protein could potentially lead to undesirable physiological disruption, even in the absence of antibody-mediated cytotoxicity. We have shown that rat anti-CLDN1 mAb OM-7D3-B3 does not cause any toxicity in immunocompetent mice (21); this is likely also to be the case for the humanized anti-CLDN1 mAb H3L3. Notably, the humanized antibodies did not exert any cellular toxicity in vitro (data not shown). We did not observe any overt toxic effects in human liver chimeric mice, either (FIG. 5B).

In conclusion, we report successful humanization of the rat anti-CLDN1 mAb OM-7D3-B3, without any loss of anti-HCV function. Further evaluation of this antibody in pre-clinical efficacy and toxicity studies in suitable animal models will pave the way for clinical trials in humans. Anti-receptor antibodies such as H3L3 could provide an alternative approach for HCV therapy, aimed at patients who do not respond to current therapies or to prevent liver graft infection. Moreover, the identification of CLDN1 as an entry factor for dengue virus (40, 41) also opens interesting perspectives to develop the humanized anti-CLDN1 mAb as a potential anti-dengue agent.

REFERENCES

Throughout this application, various references describe the state of the art to which this invention pertains. The disclosures of these references are hereby incorporated by reference into the present disclosure.

1. Ferenci P. Treatment of hepatitis C in difficult-to-treat patients. Nat Rev Gastroenterol Hepatol 2015; 12:284-292.
2. Goossens N, Negro F. Is genotype 3 of the hepatitis C virus the new villain? Hepatology 2014; 59:2403-2412.
3. Kanwal F, Kramer J R, Ilyas J, Duan Z, El-Serag H B. HCV genotype 3 is associated with an increased risk of cirrhosis and hepatocellular cancer in a national sample of U.S. Veterans with HCV. Hepatology 2014; 60:98-105.
4. Chung R T, Baumert T F. Curing chronic hepatitis C—the arc of a medical triumph. N Engl J Med 2014; 370:1576-1578.
5. Pileri P, Uematsu Y, Campagnoli S, Galli G, Falugi F, Petracca R, Weiner A J, et al. Binding of hepatitis C virus to CD81. Science 1998; 282:938-941.
6. Scarselli E, Ansuini H, Cerino R, Roccasecca R M, Acali S, Filocamo G, Traboni C, et al. The human scavenger receptor class B type I is a novel candidate receptor for the hepatitis C virus. EMBO J 2002; 21:5017-5025.
7. Evans M J, von Hahn T, Tscherne D M, Syder A J, Panis M, Wolk B, Hatziioannou T, et al. Claudin-1 is a hepatitis C virus co-receptor required for a late step in entry. Nature 2007; 446:801-805.
8. Ploss A, Evans M J, Gaysinskaya V A, Panis M, You H, de Jong Y P, Rice C M. Human occludin is a hepatitis C virus entry factor required for infection of mouse cells. Nature 2009; 457:882-886.
9. Lupberger J, Zeisel M B, Xiao F, Thumann C, Fofana I, Zona L, Davis C, et al. EGFR and EphA2 are host factors for hepatitis C virus entry and possible targets for antiviral therapy. Nat Med 2011; 17:589-595.
10. Sainz B, Jr., Barretto N, Martin D N, Hiraga N, Imamura M, Hussain S, Marsh K A, et al. Identification of the Niemann-Pick C1-like 1 cholesterol absorption receptor as a new hepatitis C virus entry factor. Nat Med 2012; 18:281-285.
11. Zona L, Lupberger J, Sidahmed-Adrar N, Thumann C, Harris H J, Barnes A, Florentin J, et al. HRas signal transduction promotes hepatitis C virus cell entry by triggering assembly of the host tetraspanin receptor complex. Cell Host Microbe 2013; 13:302-313.
12. Martin D N, Uprichard S L. Identification of transferrin receptor 1 as a hepatitis C virus entry factor. Proc Natl Acad Sci USA 2013; 110:10777-10782.
13. Bartosch B, Vitelli A, Granier C, Goujon C, Dubuisson J, Pascale S, Scarselli E, et al. Cell entry of hepatitis C virus requires a set of co-receptors that include the CD81 tetraspanin and the SR-B1 scavenger receptor. J Biol Chem 2003; 278:41624-41630.
14. Cormier E G, Tsamis F, Kajumo F, Durso R J, Gardner J P, Dragic T. CD81 is an entry coreceptor for hepatitis C virus. Proc Natl Acad Sci USA 2004; 101:7270-7274.
15. Meuleman P, Hesselgesser J, Paulson M, Vanwolleghem T, Desombere I, Reiser H, Leroux-Roels G. Anti-CD81 antibodies can prevent a hepatitis C virus infection in vivo. Hepatology 2008; 48:1761-1768.
16. Zhang J, Randall G, Higginbottom A, Monk P, Rice C M, McKeating J A. CD81 is required for hepatitis C virus glycoprotein-mediated viral infection. J Virol 2004; 78:1448-1455.
17. Catanese M T, Ansuini H, Graziani R, Huby T, Moreau M, Ball J K, Paonessa G, et al. Role of scavenger receptor class B type I in hepatitis C virus entry: kinetics and molecular determinants. J Virol 2010; 84:34-43.
18. Lacek K, Vercauteren K, Grzyb K, Naddeo M, Verhoye L, Slowikowski M P, Fafi-Kremer S, et al. Novel human SR-BI antibodies prevent infection and dissemination of HCV in vitro and in humanized mice. J Hepatol 2012; 57:17-23.
19. Vercauteren K, Van Den Eede N, Mesalam A A, Belouzard S, Catanese M T, Bankwitz D, Wong-Staal F, et al. Successful anti-scavenger receptor class B type I (SR-BI) monoclonal antibody therapy in humanized mice after challenge with HCV variants with in vitro resistance to SR-BI-targeting agents. Hepatology 2014; 60:1508-1518.

20. Fofana I, Krieger S E, Grunert F, Glauben S, Xiao F, Fafi-Kremer S, Soulier E, et al. Monoclonal anti-claudin 1 antibodies prevent hepatitis C virus infection of primary human hepatocytes. Gastroenterology 2010; 139:953-964, 964 e951-954.
21. Mailly L, Xiao F, Lupberger J, Wilson G K, Aubert P, Duong F H, Calabrese D, et al. Clearance of persistent hepatitis C virus infection in humanized mice using a claudin-1-targeting monoclonal antibody. Nat Biotechnol 2015; 33:549-554.
22. Xiao F, Fofana I, Thumann C, Mailly L, Alles R, Robinet E, Meyer N, et al. Synergy of entry inhibitors with direct-acting antivirals uncovers novel combinations for prevention and treatment of hepatitis C. Gut 2015; 64:483-494.
23. Xiao F, Fofana I, Heydmann L, Barth H, Soulier E, Habersetzer F, Doffoel M, et al. Hepatitis C virus cell-cell transmission and resistance to direct-acting antiviral agents. PLoS Pathog 2014; 10:e1004128.
24. Krieger S E, Zeisel M B, Davis C, Thumann C, Harris H J, Schnober E K, Mee C, et al. Inhibition of hepatitis C virus infection by anti-claudin-1 antibodies is mediated by neutralization of E2-CD81-claudin-1 associations. Hepatology 2010; 51:1144-1157.
25. Zheng A, Yuan F, Li Y, Zhu F, Hou P, Li J, Song X, et al. Claudin-6 and claudin-9 function as additional coreceptors for hepatitis C virus. J Virol 2007; 81:12465-12471.
26. Meertens L, Bertaux C, Cukierman L, Cormier E, Lavillette D, Cosset F L, Dragic T. The tight junction proteins claudin-1, -6, and -9 are entry cofactors for hepatitis C virus. J Virol 2008; 82:3555-3560.
27. Haid S, Grethe C, Dill M T, Heim M, Kaderali L, Pietschmann T. Isolate-dependent use of claudins for cell entry by hepatitis C virus. Hepatology 2014; 59:24-34.
28. Fofana I, Zona L, Thumann C, Heydmann L, Durand S C, Lupberger J, Blum H E, et al. Functional analysis of claudin-6 and claudin-9 as entry factors for hepatitis C virus infection of human hepatocytes by using monoclonal antibodies. J Virol 2013; 87:10405-10410.
29. Kabat E A, Wu T T. Identical V region amino acid sequences and segments of sequences in antibodies of different specificities. Relative contributions of VH and VL genes, minigenes, and complementarity-determining regions to binding of antibody-combining sites. J Immunol 1991; 147:1709-1719.
30. Jones P T, Dear P H, Foote J, Neuberger M S, Winter G. Replacing the complementarity-determining regions in a human antibody with those from a mouse. Nature 1986; 321:522-525.
31. Verhoeyen M, Milstein C, Winter G. Reshaping human antibodies: grafting an antilysozyme activity. Science 1988; 239:1534-1536.
32. Mee C J, Harris H J, Farquhar M J, Wilson G, Reynolds G, Davis C, van ISC, et al. Polarization restricts hepatitis C virus entry into HepG2 hepatoma cells. J Virol 2009; 83:6211-6221.
33. Pestka J M, Zeisel M B, Blaser E, Schurmann P, Bartosch B, Cosset F L, Patel A H, et al. Rapid induction of virus-neutralizing antibodies and viral clearance in a single-source outbreak of hepatitis C. Proc Natl Acad Sci USA 2007; 104:6025-6030.
34. Fafi-Kremer S, Fofana I, Soulier E, Carolla P, Meuleman P, Leroux-Roels G, Patel A H, et al. Viral entry and escape from antibody-mediated neutralization influence hepatitis C virus reinfection in liver transplantation. J Exp Med 2010; 207:2019-2031.
35. Koutsoudakis G, Kaul A, Steinmann E, Kallis S, Lohmann V, Pietschmann T, Bartenschlager R. Characterization of the early steps of hepatitis C virus infection by using luciferase reporter viruses. J Virol 2006; 80:5308-5320.
36. Witteveldt J, Evans M J, Bitzegeio J, Koutsoudakis G, Owsianka A M, Angus A G, Keck Z Y, et al. CD81 is dispensable for hepatitis C virus cell-to-cell transmission in hepatoma cells. J Gen Virol 2009; 90:48-58.
37. Prichard M N, Shipman C, Jr. A three-dimensional model to analyze drug-drug interactions. Antiviral Res 1990; 14:181-205.
38. Mercer D F, Schiller D E, Elliott J F, Douglas D N, Hao C, Rinfret A, Addison W R, et al. Hepatitis C virus replication in mice with chimeric human livers. Nat Med 2001; 7:927-933.
39. Paciello R, Urbanowicz R A, Riccio G, Sasso E, McClure P C, Zambrano N, Ball J K, et al. Novel human anti-Claudin 1 monoclonal antibodies inhibit HCV infection and may synergize with anti-SRB1 mAb. J Gen Virol 2015.
40. Che P, Tang H, Li Q. The interaction between claudin-1 and dengue viral prM/M protein for its entry. Virology 2013; 446:303-313.
41. Gao F, Duan X, Lu X, Liu Y, Zheng L, Ding Z, Li J. Novel binding between pre-membrane protein and claudin-1 is required for efficient dengue virus entry. Biochem Biophys Res Commun 2010; 391:952-957.

Example 2

Preclinical Development of a Claudin-1 Specific Monoclonal Antibody for Treatment of Nonalcoholic Steatohepatitis (NASH)

NASH, the Next Global Epidemic.

Nonalcoholic fatty liver disease (NAFLD) occurs when excess fat accumulates in liver cells in people who consume little or no alcohol. NAFLD is associated with various metabolic risk factors, such as obesity and diabetes. NAFLD can progress to advanced liver disease and liver cancer (1). Simple fat accumulation, referred to as steatosis, accounts for 80-90% of NAFLD cases, while liver fat accumulation and inflammation, referred to as NASH, accounts for 10-20% (2). NASH represents the most extreme form of NAFLD and 4-22% of HCC cases are NASH-induced in Western countries. Moreover, NAFLD-related cirrhosis accounts for 15-30% of cirrhosis-induced HCC worldwide (3). As NAFLD has reached epidemic proportions and is becoming the most common cause for chronic liver disease, NASH will likely replace chronic hepatitis C as leading indication for liver cirrhosis and liver transplantation in this decade. Despite this alarming trend, effective treatment is lacking and continues to rely on dietary interventions and physical exercise, known to be of limited effect. Hence, there is an urgent need for safe pharmacologic therapy that successfully reverses or prevents progression of liver injury and fibrosis in patients with NASH (4). Some compounds for the treatment of NASH have reached clinical development—GFT505, GENFIT; OCA, Intercept; Aramchol—arachidyl amido cholanoic acid, Galmed Pharmaceuticals Ltd. However, so far efficacy has been limited to improvements in clinical chemistry (liver function tests). Effects on fibrosis and disease progression are minimal and their safety has limitations (5).

Identification of Lead Humanized CLDN1 mAb for Preclinical and Clinical Development.

To determine the lead humanized CLDN1 mAb for further development we assessed the performance of our panel of nine humanized CLDN1 mAb isotypes in our liver cell-based system. Huh7.5.1 were differentiated into hepatocyte-like Huh7.5.1dif cells, persistently infected with HCV Jc1 to induce the liver disease progression signature. Cells were treated with monoclonal mAbs at day 7 for 3 days. Treatment with all nine CLDN1 mAb isotypes resulted in a significant reversal of the liver disease progression signature at concentrations that do not affect HCV load. This demonstrates that the CLDN1 mAbs act on the liver disease progression signature independent its antiviral activity and reverts the expression of the liver disease progression signature independent of the etiology (virus, alcohol, NASH). The H3L3 isotype was chosen as the lead CLDN1 mAb for further development due to its strong effect on the liver disease progression signature and detailed characterization in cell culture and animal models (Colpitts et al., Gut 2016 in press).

Validation of Humanized CLDN1 mAb (H3L3) as a Lead Candidate Compound for Treatment of Chronic Liver Disease and NASH.

Taking advantage of our patient liver disease progression signature-based liver model systems, we assessed the efficiency of the humanized CLDN1 mAb at reversing the liver disease progression signature induced by various etiologies (HCV, HBV, alcohol and NASH). The humanized CLDN1 mAb (H3L3) was effective at reversing the liver disease progression signature in the NASH model (FFA) as well as for other etiologies confirming its potential as a therapeutic candidate for NASH. Most strikingly, the CLDN1 mAb was much more potent at reversing the liver disease progression signature when compared to the most advanced molecules in clinical development for NASH treatment (GTF505 and OCA) (data not shown).

In Vivo Proof-of-Concept for Anti-Claudin for Treatment of Chronic Liver Disease/NASH To perform proof-of concept studies in mouse models we generated a murinized antibody targeting the human Claudin-1. The mouse CLDN1-specific mAb mIgG3 binds to both mouse and human CLDN1 albeit with reduced affinity to mouse Claudin-1. Importantly, treatment of hepatocyte-like cells with the murinized CLDN1 mAb resulted in reversal of the liver disease progression signature validating this antibody for further application in in vitro and in vivo studies. Pharmacokinetic studies in mice revealed a half-life of 7.7 days (data not shown). Treatment with both the humanized and murinized CLDN1 mAb result in suppression of the liver disease progression signature (data not shown).

We next performed a study to address the effect of the CLDN1 mAb on liver disease progression using an in vivo mouse model. Liver disease was induced in C3H/He mice by a single administration of diethylnitrosamine (DEN) which resulted in microvacuolar steatosis affecting around 6% of the liver (data not shown). To assess the effect of the mAb on liver disease progression, mice were given a murinized CLDN1 mAb mIgG3 for five weeks. Whereas all control animals continued to develop liver steatosis at week 23 post DEN administration, a marked and significant reduction in steatosis was observed in mice treated with the CLDN1-specific mAb (data not shown). Since fibrosis development was minimal or absent in this model, the effect of the mAb on fibrosis could not be assessed. The effect on fibrosis will be evaluated in the high fat diet models as outlined in the sections below. This pilot study demonstrates that the mAb reverts liver disease progression including treatment of steatosis in vivo. Consistent with the previously described excellent in vivo safety profile of the mAb (12) and we did not observe any detectable adverse effects.

REFERENCES

1. Musso, G., Cassader, M. & Gambino, R. Non-alcoholic steatohepatitis: emerging molecular targets and therapeutic strategies. Nat. Rev. Drug Discov., 2016, 15:249-274
2. Hashimoto, E., Taniai, M. & Tokushige, K. Characteristics and diagnosis of NAFLD/NASH. J. Gastroenterol. Hepatol., 2013, 28 Suppl 4:64-70
3. Michelotti, G. A., Machado, M. V. & Diehl, A. M. NAFLD, NASH and liver cancer. Nat. Rev. Gastroenterol. Hepatol., 2013, 10:656-665
4. Fuchs, M. New medical treatment strategies for nonalcoholic steatohepatitis. Curr. Treat. Options Gastroenterol., 2015, 13:259-273
5. Ratziu, V., et al. Elafibranor, an Agonist of the Peroxisome Proliferator-Activated Receptor-alpha and -delta, Induces Resolution of Nonalcoholic Steatohepatitis Without Fibrosis Worsening. Gastroenterol., 2016, 150:1147-1159

The invention claimed is:

1. An anti-Claudin-1 humanized antibody comprising all the Complementary Determining Regions (CDRs) of rat monoclonal antibody OM-7D3-B3, wherein the variable heavy chain of OM-7D3-B3 consists of amino acid sequence SEQ ID NO: 3 and the variable light chain of OM-7D3-B3 consists of amino acid sequence SEQ ID NO: 4, said anti-Claudin-1 humanized antibody further comprising:
   a) at least one antibody variable heavy chain (VH) consisting of the amino acid sequence of SEQ ID NO: 1, or
   b) at least one antibody variable light chain (VL) consisting of the amino acid sequence of SEQ ID NO: 2, or
   c) at least one antibody variable heavy chain (VH) consisting of the amino acid sequence of SEQ ID NO: 1, and at least one antibody variable light chain (VL) consisting of the amino acid sequence of SEQ ID NO: 2.

2. The anti-Claudin-1 humanized antibody according to claim 1 wherein:
   a) both variable heavy chains (VH) of said anti-Claudin-1 humanized antibody consist of the amino acid sequence of SEQ ID NO: 1, or
   b) both variable light chains (VL) of said anti-Claudin-1 humanized antibody consist of the amino acid sequence of SEQ ID NO: 2, or
   c) both variable heavy chains (VH) of said anti-Claudin-1 humanized antibody consist of the amino acid sequence of SEQ ID NO: 1, and both variable light chains (VL) of said anti-Claudin-1 humanized antibody consist of the amino acid sequence of SEQ ID NO: 2.

3. The anti-Claudin-1 humanized antibody according to claim 1, wherein said humanized antibody is a full antibody having an isotype selected from the group consisting of IgG1, IgG2, IgG3, and IgG4.

4. A fragment of the anti-Claudin-1 humanized antibody according to claim 1, wherein said fragment is selected from the group consisting of Fv, Fab, F(ab')2, Fab', dsFv, scFv, sc(Fv)2 and diabodies.

5. The anti-Claudin-1 humanized antibody according to claim 1, wherein said anti-Claudin-1 humanized antibody is conjugated to a cytotoxic moiety.

6. A method of treating a viral infection in a patient in need thereof comprising a step of: administering to the patient a therapeutically effective amount of the anti-Claudin-1 humanized antibody according to claim 1.

7. A method of treating a colorectal cancer or hepatocellular carcinoma in a patient in need thereof comprising a step of: administering to the patient a therapeutically effective amount of the anti-Claudin-1 humanized antibody according to claim 1.

8. A method of treating a fatty liver disease (FLD) in a patient in need thereof comprising a step of: administering to the patient a therapeutically effective amount of the anti-Claudin-1 humanized antibody according to claim 1.

9. The method of claim 8, wherein the fatty liver disease (FLD) is a nonalcoholic fatty liver disease (NAFLD) or a non-alcoholic steatohepatitis (NASH).

10. A pharmaceutical composition comprising the anti-Claudin-1 humanized antibody according to claim 1, and a pharmaceutically acceptable carrier.

11. The anti-Claudin-1 humanized antibody according to claim 1, wherein:

a) at least one antibody variable heavy chain (VH) consists of the amino acid sequence of SEQ ID NO: 1 and at least one antibody variable light chain (VL) consists of amino acid sequence SEQ ID NO: 10 or amino acid sequence SEQ ID NO: 12 , or
b) at least one antibody variable light chain (VL) consists of the amino acid sequence of SEQ ID NO: 2 and at least one antibody variable heavy chain (VH) consists of amino acid sequence SEQ ID NO: 9 or amino acid sequence SEQ ID NO: 11, or
c) at least one antibody variable heavy chain (VH) consists of the amino acid sequence of SEQ ID NO: 1, and at least one antibody variable light chain (VL) consists of the amino acid sequence of SEQ ID NO: 2.

12. The anti-Claudin-1 humanized antibody according to claim 2, wherein:
a) both variable heavy chains (VH) of said anti-Claudin-1 humanized antibody consist of the amino acid sequence of SEQ ID NO: 1 and both variable light chains (VL) of said anti-Claudin-1 humanized antibody consist of amino acid sequence SEQ ID NO: 10; or
a') both variable heavy chains (VH) of said anti-Claudin-1 humanized antibody consist of the amino acid sequence of SEQ ID NO: 1 and both variable light chains (VL) of said anti-Claudin-1 humanized antibody consist of amino acid sequence SEQ ID NO: 12; or
b) both variable light chains (VL) of said anti-Claudin-1 humanized antibody consist of the amino acid sequence of SEQ ID NO: 2 and both variable heavy chains (VH) of said anti-Claudin-1 humanized antibody consist of sequence SEQ ID NO: 9; or
b') both variable light chains (VL) of said anti-Claudin-1 humanized antibody consist of the amino acid sequence of SEQ ID NO: 2 and both variable heavy chains (VH) of said anti-Claudin-1 humanized antibody consist of sequence SEQ ID NO: 11; or
c) both variable heavy chains (VH) of said anti-Claudin-1 humanized antibody consist of the amino acid sequence of SEQ ID NO: 1 and both variable light chains (VL) of said anti-Claudin-1 humanized antibody consist of the amino acid sequence of SEQ ID NO: 2.

* * * * *

UNITED STATES PATENT AND TRADEMARK OFFICE
CERTIFICATE OF CORRECTION

PATENT NO. : 10,851,160 B2
APPLICATION NO. : 16/086934
DATED : December 1, 2020
INVENTOR(S) : Thomas Baumert and Rajeevkumar Tawar Page 1 of 1

It is certified that error appears in the above-identified patent and that said Letters Patent is hereby corrected as shown below:

In the Claims

In Column 45, Line 37 (Claim 1), replace "Complementary Determining Regions (CDRs)" with -- Complementarity Determining Regions (CDRs) --.

Signed and Sealed this
Eighth Day of August, 2023

Katherine Kelly Vidal
*Director of the United States Patent and Trademark Office*